(12) United States Patent
Varadan et al.

(10) Patent No.: US 12,138,058 B2
(45) Date of Patent: Nov. 12, 2024

(54) WEARABLE CONGESTIVE HEART FAILURE MANAGEMENT SYSTEM

(71) Applicant: NANOWEAR INC., Brooklyn, NY (US)

(72) Inventors: Vijay Varadan, State College, PA (US); Pratyush Rai, State College, PA (US); Se Chang Oh, State College, PA (US); Prashanth Shyam Kumar, State College, PA (US); Mouli Ramasamy, State College, PA (US)

(73) Assignee: NANOWEAR INC., Brooklyn, NY (US)

( * ) Notice: Subject to any disclaimer, the term of this patent is extended or adjusted under 35 U.S.C. 154(b) by 870 days.

(21) Appl. No.: 17/174,156

(22) Filed: Feb. 11, 2021

(65) Prior Publication Data

US 2021/0177335 A1 Jun. 17, 2021

Related U.S. Application Data

(63) Continuation of application No. 15/967,792, filed on May 1, 2018, now Pat. No. 10,959,634.

(Continued)

(51) Int. Cl.
*A61B 5/282* (2021.01)
*A61B 5/00* (2006.01)
(Continued)

(52) U.S. Cl.
CPC ............ *A61B 5/282* (2021.01); *A61B 5/0022* (2013.01); *A61B 5/0205* (2013.01); *A61B 5/021* (2013.01); *A61B 5/02108* (2013.01); *A61B 5/0531* (2013.01); *A61B 5/0535* (2013.01); *A61B 5/0816* (2013.01); *A61B 5/1116* (2013.01); *A61B 5/1135* (2013.01); *A61B 5/339* (2021.01);
(Continued)

(58) Field of Classification Search
CPC ....... A61B 5/022; A61B 5/0205; A61B 5/021; A61B 5/0816; A61B 5/1116; A61B 5/282; A61B 5/6831; A61B 7/04; A61B 2562/0247; G16H 40/63
See application file for complete search history.

(56) References Cited

U.S. PATENT DOCUMENTS 4,367,752 A 1/1983 Jimenez et al.
4,572,197 A 2/1986 Moore et al.
(Continued)

OTHER PUBLICATIONS

C. W. Yancy et al., "2013 ACCF/AHA Guideline for the Management of Heart Failure: A Report of the American College of Cardiology Foundation/American Heart Association Task Force on Practice Guidelines," Journal of the American College of Cardiology, vol. 62, pp. e147-e239, Oct. 15, 2013.
(Continued)

*Primary Examiner* — Christopher A Flory
(74) *Attorney, Agent, or Firm* — Davidson Kappel LLC

(57) ABSTRACT

A non-invasive, wearable and portable medical device for evaluation and monitoring the heart condition for patients with congestive heart failure and a CHF management system is provided comprising a wearable textile-based device utilizing physiologic and biometric sensors, a Signal Acquisition Unit, and a monitoring system executing a suite of software algorithms to monitor and evaluate patients with CHF.

18 Claims, 25 Drawing Sheets

Related U.S. Application Data

(60) Provisional application No. 62/500,085, filed on May 2, 2017.

(51) Int. Cl.

| | |
|---|---|
| *A61B 5/02* | (2006.01) |
| *A61B 5/0205* | (2006.01) |
| *A61B 5/021* | (2006.01) |
| *A61B 5/0531* | (2021.01) |
| *A61B 5/0535* | (2021.01) |
| *A61B 5/08* | (2006.01) |
| *A61B 5/11* | (2006.01) |
| *A61B 5/113* | (2006.01) |
| *A61B 5/339* | (2021.01) |
| *A61B 5/341* | (2021.01) |
| *A61B 5/349* | (2021.01) |
| *A61B 7/04* | (2006.01) |
| *G16H 40/63* | (2018.01) |
| *G16H 50/20* | (2018.01) |

(52) U.S. Cl.
CPC .............. *A61B 5/341* (2021.01); *A61B 5/349* (2021.01); *A61B 5/4809* (2013.01); *A61B 5/6823* (2013.01); *A61B 5/6831* (2013.01); *A61B 5/7239* (2013.01); *A61B 5/7275* (2013.01); *A61B 7/04* (2013.01); *G16H 40/63* (2018.01); *G16H 50/20* (2018.01); *A61B 5/02028* (2013.01); *A61B 2505/07* (2013.01); *A61B 2562/0204* (2013.01); *A61B 2562/0219* (2013.01); *A61B 2562/0247* (2013.01); *A61B 2562/028* (2013.01); *A61B 2562/0285* (2013.01); *A61B 2562/04* (2013.01)

(56) References Cited

U.S. PATENT DOCUMENTS

| | | | |
|---|---|---|---|
| 5,007,427 | A | 4/1991 | Suzuki et al. |
| 5,078,134 | A | 1/1992 | Heilman et al. |
| 5,353,793 | A | 10/1994 | Bornn |
| 5,501,229 | A | 3/1996 | Sekler et al. |
| 5,749,365 | A | 5/1998 | Magill |
| 5,802,607 | A | 9/1998 | Triplette |
| 5,853,005 | A | 12/1998 | Scanlon |
| 6,047,203 | A | 4/2000 | Sackner et al. |
| 6,662,032 | B1 | 12/2003 | Gavish et al. |
| 6,687,523 | B1 | 2/2004 | Jayaramen et al. |
| 7,136,693 | B2 | 11/2006 | Brodnick |
| 7,319,895 | B2 | 1/2008 | Klefstad-Sillonville et al. |
| 7,354,877 | B2 | 4/2008 | Rosenberger et al. |
| 7,390,760 | B1 | 7/2008 | Chen et al. |
| 7,559,902 | B2 | 7/2009 | Ting et al. |
| 7,592,276 | B2 | 9/2009 | Hill |
| 7,857,777 | B2 | 12/2010 | Larson et al. |
| 7,862,624 | B2 | 1/2011 | Tran |
| 7,871,700 | B2 | 1/2011 | Poulin et al. |
| 8,348,841 | B2 | 1/2013 | Varadan |
| 10,478,327 | B2 | 11/2019 | Liu |
| 2005/0034485 | A1 | 2/2005 | Klefstad-Sillonville et al. |
| 2006/0024499 | A1 | 2/2006 | Kim et al. |
| 2006/0175581 | A1 | 8/2006 | Douglas et al. |
| 2006/0252999 | A1 | 11/2006 | Devaul et al. |
| 2006/0282021 | A1 | 12/2006 | Devaul et al. |
| 2007/0049842 | A1 | 3/2007 | Hill et al. |
| 2007/0120297 | A1 | 5/2007 | Weider |
| 2007/0293781 | A1 | 12/2007 | Sims et al. |
| 2008/0027341 | A1* | 1/2008 | Sackner ............... A61B 5/6804 600/509 |
| 2008/0083740 | A1 | 4/2008 | Kaiserman et al. |
| 2008/0139911 | A1 | 6/2008 | Chandrasekaran et al. |
| 2008/0287769 | A1 | 11/2008 | Kurzweil et al. |
| 2009/0024017 | A1 | 1/2009 | Ruffini et al. |
| 2009/0088652 | A1 | 4/2009 | Tremblay |
| 2009/0131759 | A1 | 5/2009 | Sims et al. |
| 2009/0306485 | A1 | 12/2009 | Bell |
| 2010/0185398 | A1 | 7/2010 | Berns et al. |
| 2010/0198038 | A1 | 8/2010 | Nagata et al. |
| 2010/0273049 | A1 | 10/2010 | Vidal et al. |
| 2010/0274100 | A1 | 10/2010 | Bahar et al. |
| 2011/0004088 | A1 | 1/2011 | Grossman |
| 2011/0060215 | A1* | 3/2011 | Tupin, Jr. ............. A61B 5/1075 600/407 |
| 2011/0260115 | A1 | 10/2011 | Kim |
| 2013/0281795 | A1 | 10/2013 | Varadan |
| 2013/0281815 | A1 | 10/2013 | Varadan |
| 2014/0196190 | A1 | 7/2014 | Brown |
| 2014/0296653 | A1 | 10/2014 | Jenkins, III |
| 2014/0296761 | A1 | 10/2014 | Yamamoto et al. |
| 2014/0318699 | A1* | 10/2014 | Longinotti-Buitoni ...................... H05K 1/095 156/247 |
| 2014/0378812 | A1 | 12/2014 | Saroka et al. |
| 2015/0250420 | A1* | 9/2015 | Longinotti-Buitoni ...................... A61B 5/1135 600/534 |
| 2016/0183835 | A1 | 6/2016 | Varadan |
| 2017/0119255 | A1* | 5/2017 | Mahajan .................. A61B 7/00 |
| 2017/0196513 | A1* | 7/2017 | Longinotti-Buitoni ...................... D06P 1/5285 |
| 2017/0202724 | A1 | 7/2017 | De Rossi et al. |
| 2018/0000367 | A1* | 1/2018 | Longinotti-Buitoni ...................... A41D 13/1281 |
| 2018/0325407 | A1* | 11/2018 | Varadan ................. A61B 5/339 |
| 2019/0282164 | A1 | 9/2019 | Saroka et al. |

OTHER PUBLICATIONS

Pinamonti B et al. "Restrictive left ventricular filling pattern in dilated cardiomyopathy assessed by Doppler echocardiography: clinical, echocardiographic and hemodynamic correlations and prognostic implications" Heart Muscle Disease Study Group. J Am CollCardiol. Sep. 1993 22(3):808-15.

Temporelli PL et al., "Doppler echocardiography in advanced systolic heart failure: a noninvasive alternative to Swan-Ganz catheter" Circ Heart Fail. May 2010 3(3):387-94).

Murphy RT et al., Genetics and cardiomyopathy: where are we now?, Cleve Clin J Med. Jun. 2005. 72(6):abstract.

Huei et al., "Develop an efficient Electrode to detect ECG signal" download from the internet prior to Aug. 19, 2011.

Lindenfeld J et al. "HFSA 2010 Comprehensive Heart Failure Practice Guideline" J Card Fail. Jun. 2010. abstract.

Indiareport, "Now a vest that tracks medical condition" dated Oct. 12, 2011, http://www.indiareport.com/news-details/print_news.php?id=11 . . . accessed Oct. 13, 2011 (1 page).

Jahrsdoerfer et al., "Clinical Usefulness of the EASI 12-Lead Continuous Electrocardiogrammonitoring System" CritCare Nurse 2005; 25:28-37, cnn.aacnjournals.org, accessed on Oct. 25, 2012.

Dickstein K.et al. "ESC Guidelines for the diagnosis and treatment of acute and chronic heart failure 2008: The Task Force for the Diagnosis and Treatment of Acute and Chronic Heart Failure 2008 of the European Society of Cardiology. Developed in collaboration with the Heart Failure Association of the ESC (HFA) and endorsed by the European Society of Intensive Care Medicine (ESICM)" Eur Heart J. Oct. 2008. 29(19):2388-442.

Pratyush Rai et al. "Nano-Bio-Textile Sensors with Mobile Wireless Platform for Wearable Health Monitoring of Neurological and Cardiovascular Disorders," J. Electrochem. Soc. 2014 volume 161, issue 2, B3116-B3150.

Scanlon, "Acoustic Sensor Pad for Physiology Monitoring" Proceedings—19th International Conference—IEEE/EMBS Oct. 30-Nov. 2, 1997 (4 pages).

Varadan et al. "e-bra with Nanosensors for Real Time Cardiac Health Monitoring and Smartphone Communication" Journal of Nanotechnology in Engineering and Medicine, May 1, 2011, vol. 2 (7 pages).

(56) References Cited

OTHER PUBLICATIONS

Varadan et al. "e-Nanoflex Sensor System: Smartphone-Based Roaming Health Monitor" Journal of Nanotechnology in Engineering and Medicine Feb. 1, 2010, vol. 2 (11 pages).

Varadan, "Wireless Point-of-Care Diagnosis for Sleep Disorder With Dry Nanowire Electrodes" Journal of Nanotechnology in Engineering and Medicine Aug. 2010, vol. 1 (11 pages).

Varadan, "An EKG in your Underwear. Nanostructured sensors, smartphones, and cloud computing promise a new platform everyday medical morning." Mechanical Engineering Magazine, http://memagazine.asme.org/Articles/2011/October/EKG_Underwear.cfm? PrintPage=yes, accessed Oct. 14, 2011 (5pages).

Vijay K. Varadan et al. "E-bra with nanosensors, smart electronics and smart phone communication network for heart rate monitoring" Proc. SPIE 7980, Nanosensors, Biosensors, and Info-Tech Sensors and Systems 2011, 79800S (Apr. 13, 2011); doi:10. 1117/12.885649.

Rai, Pratyush, "Hybrid Nanostructured Textile Bioelectrode for Unobtrusive Health Monitoring" (Aug. 2013). Theses and Dissertations. 893 (Year: 2013).

* cited by examiner

| Composite packet – Generated every 20 ms | Byte 1-9 – ECG 1 | Byte 10-18 – ECG 2 | Byte 19-27 – ICG 1 | Byte 28-36 – ICG 2 | Byte 37-56 – Sound | Byte 57-58 – Accel X | Byte 59-60 – Accel Y | Byte 61-62 – Accel Z | Byte 63-71 – Status 1 | Byte 72-80 – Status 2 |

| Channel Name | Bits/Sample | Sampling Frequency (Hz) | Bytes/Sample | Bytes/Composite packet | Bytes/second |
| --- | --- | --- | --- | --- | --- |
| ECG 1 | 24 | 150 | 3 | 9 | 450 |
| ECG 2 | 24 | 150 | 3 | 9 | 450 |
| ICG 1 | 24 | 150 | 3 | 9 | 450 |
| ICG 2 | 24 | 150 | 3 | 9 | 450 |
| Sound | 16 | 500 | 2 | 20 | 1000 |
| Accelerometer X | 16 | 50 | 2 | 2 | 100 |
| Accelerometer Y | 16 | 50 | 2 | 2 | 100 |
| Accelerometer Z | 16 | 50 | 2 | 2 | 100 |
| Status 1 | 24 | 150 | 3 | 9 | 450 |
| Status 2 | 24 | 150 | 3 | 9 | 450 |
| Total | | | | 80 | 4000 |

WEARABLE CONGESTIVE HEART FAILURE MANAGEMENT SYSTEM

This application is a continuation of U.S. application Ser. No. 15/967,792, filed May 1, 2018, which claims the benefit of U.S. Provisional Patent Application No. 62/500,085, filed May 2, 2017, entitled WEARABLE CONGESTIVE HEART FAILURE MANAGEMENT SYSTEM, the entire disclosures of which are hereby incorporated by reference.

FIELD OF INVENTION

The present invention relates to the field of non-invasive, wearable and portable medical devices, methods, systems and apparatus, including but not limited, for monitoring physiological parameters.

BACKGROUND

Congestive Heart Failure (CHF) is a complex clinical syndrome that results from any structural or functional impairment of the ventricular chamber of the heart that affects the filling or ejection of blood in a cardiac cycle. CHF manifests clinically as fatigue and dyspnea (shortness of breath). This may in turn result in exercise intolerance and fluid retention. Fluid retention leads to pulmonary congestion and/or peripheral edema. Cardiac rhythm abnormalities are very common among CHF patients. Any new abnormalities that arise in a patient with fluid decompensation prolongs hospitalization as well as increases mortality rates.

Within 5 years of a CHF diagnosis, the mortality rate is 50%. The 30 day, 1-year and 5-year fatality rates after CHF related hospitalization were 10.4%, 22% and 42.3% respectively. Post discharge mortality increased from 4.3% to 6.4% between 1993 and 2005. In 2006, the number of deaths with a mention of CHF was as high as it was in 1995. One out of every nine mortalities in the US has CHF mentioned as a cause. CHF related deaths are approximately 7% of all cardiovascular diseases. In the US, CHF related costs exceeded $30 billion in 2013. The average cost per patient for CHF related hospitalization was $23,077. Hospitalization after a CHF diagnosis happens at least once in 83% of the patients and up to four times in 43% of the patients. See C. W. Yancy, M. Jessup, B. Bozkurt, J. Butler, D. E. Casey Jr, M. H. Drazner, et al., "2013 ACCF/AHA Guideline for the Management of Heart Failure: A Report of the American College of Cardiology Foundation/American Heart Association Task Force on Practice Guidelines," Journal of the American College of Cardiology, vol. 62, pp. e147-e239, Oct. 15, 2013.

The current diagnostic tests and monitoring methods for CHF are limited in terms of: the need for hospitalization, in-home monitoring, obtrusiveness, and invasiveness. The common evaluation methods are categorized into: laboratory tests, imaging studies, and additional studies based on patient history.

The laboratory tests include: Complete blood count (CBC), which may indicate anemia or infection as potential causes of heart failure, Urinalysis (UA), which may reveal proteinuria, which is associated with cardiovascular disease, Serum electrolyte levels, which may be abnormal owing to causes such as fluid retention or renal dysfunction, Blood urea nitrogen (BUN) and creatinine levels, which may indicate decreased renal blood flow, Fasting blood glucose levels, because elevated levels indicate a significantly increased risk for heart failure (diabetic and nondiabetic patients), Liver function tests (LFTs), which may show elevated liver enzyme levels and indicate liver dysfunction due to heart failure, B-type natriuretic peptide (BNP) and N-terminal pro-B-type (NT-proBNP) natriuretic peptide levels, which are increased in heart failure; these measurements are closely correlated with the NYHA heart failure classification, Electrocardiogram (ECG) (12-lead), which may reveal arrhythmias, ischemia/infarction, and coronary artery disease as possible causes of heart failure.

The imaging studies include: Chest radiography (posterior-anterior, lateral), which may show pulmonary congestion, an enlarged cardiac silhouette, or other potential causes of the patient's symptoms, 2-D echocardiographic and Doppler flow ultrasonographic studies, which may reveal ventricular dysfunction and/or valvular abnormalities (Pinamonti B, Di Lenarda A, Sinagra G, Camerini F. Restrictive left ventricular filling pattern in dilated cardiomyopathy assessed by Doppler echocardiography: clinical, echocardiographic and hemodynamic correlations and prognostic implications. Heart Muscle Disease Study Group. J Am CollCardiol. 1993 Sep. 22(3):808-15, and Temporelli P L, Scapellato F, Eleuteri E, Imparato A, Giannuzzi P. Doppler echocardiography in advanced systolic heart failure: a noninvasive alternative to Swan-Ganz catheter. Circ Heart Fail. 2010 May. 3(3):387-94), Coronary arteriography in patients with a history of exertional angina or suspected ischemic LV (left ventricular) dysfunction, which may reveal coronary artery disease, Maximal exercise testing with/without respiratory gas exchange and/or blood oxygen saturation, which assesses cardiac and pulmonary function with activity, the inability to walk more than short distances, and a decreased peak oxygen consumption reflect more severe disease.

Other additional studies based on the patient history include: Screening for hemochromatosis, in which iron overload affects cardiac function, screening for sleep-disturbed breathing, which affects neurohormonal activation, screening for human immunodeficiency virus (HIV), which may result in heart failure from possible direct infectious effects, from disease treatment effects causing CAD, or from other causes, Testing for rheumatologic diseases, amyloidosis, or pheochromocytoma, all of which may cause cardiomyopathy, serum and urine electrophoresis for light-chain disease, Genetic testing for at-risk patients with a first-degree relative who has been diagnosed with a cardiomyopathy leading to heart failure, which may aid in detecting early disease onset and guide treatment (see Murphy R T, Starling R C. Genetics and cardiomyopathy: where are we now?, Cleve Clin J Med. 2005 Jun. 72(6):465-6, 469-70, 472-3 passim, and Lindenfeld J, Albert N M, Boehmer J P, Collins S P, Ezekowitz J A, Givertz M M, et al. HFSA 2010 Comprehensive Heart Failure Practice Guideline. J Card Fail. 2010 Jun. 16(6):e1-194); and holter monitoring, which may reveal arrhythmias or abnormal electrical activity (e.g., in patients with heart failure and a history of MI (Myocardial Infarction) who are being considered for electrophysiological study to document ventricular tachycardia [VT] inducibility). See [Guideline] Dickstein K, Cohen-Solal A, Filippatos G, et al. for the Task Force for the Diagnosis and Treatment of Acute and Chronic Heart Failure 2008 of the European Society of Cardiology. ESC Guidelines for the diagnosis and treatment of acute and chronic heart failure 2008: the Task Force for the Diagnosis and Treatment of Acute and Chronic Heart Failure 2008 of the European Society of Cardiology. Developed in collaboration with the Heart Failure Association of the ESC (HFA) and endorsed by the European Society of Intensive Care Medicine (ESICM). Eur Heart J. 2008 Oct. 29(19):2388-442. [Medline], and [Guideline] Lindenfeld J, Albert N M, Boehmer J P, et al, for the Heart Failure Society of America. Executive summary: HFSA 2010 comprehensive heart failure practice guideline. J Card Fail. 2010 Jun. 16(6):e1-194.)

Unobtrusive health monitoring is highly beneficial for maintaining health and independence of high risk and chronic disease patients. Intelligent wearable sensor systems with simple installation, minimal maintenance and user involvement can be the best method for ubiquitous health monitoring.

Wearable sensor systems in form of smart clothing can contribute tremendously to self-defined and autonomous (at home) living with improved quality of life. They are cost effective and provide lightweight simple technical infrastructure. Existing ambulatory recording equipment rely on conventional silver-silver chloride (Ag—AgCl) gel electrodes to perform long term monitoring. Such gel-based electrodes cannot be adapted to clothing as reusable sensors. Plain conductive textile-based electrodes do not form a good quality contact and are susceptible to ambient noise.

Nanostructured textile-based dry sensors and electrodes are better suited for long term non-invasive monitoring and measurement of physiological parameters with low baseline noise, because of their improved sensitivity and ability to perform adequately with the natural moisture level of skin. See Pratyush Rai, Sechang Oh, Prashanth Shyamkumar, Mouli Ramasamy, Robert E. Harbaugh and Vijay K. Varadan, "Nano-Bio-Textile Sensors with Mobile Wireless Platform for Wearable Health Monitoring of Neurological and Cardiovascular Disorders," J. Electrochem. Soc. 2014 volume 161, issue 2, B3116-B3150. These textile-based sensors can be seamlessly integrated into garments of daily use such as vests and brassieres. In combination with state of the art embedded wireless network devices that can communicate with a smart phone, a laptop, or directly to a remote server through the mobile network (GSM, 4G LTE, GPRS) (see US Pre-Grant Pub. No. 2013/0281815 A1), they can function as wearable wireless health diagnostic systems that are more intuitive to use.

SUMMARY OF THE INVENTION

However, existing non-invasive CHF monitoring devices are not capable of performing a multi-parametric, continuous, remote patient monitoring. In this regard, these conventional systems lack the ability to perform long term monitoring, non-reusability, lack a scalable and standardized wireless communication platform for internet-based health care services and lack adequate user-friendly design paradigms that would accommodate patients who are not technically trained.

In accordance with a first embodiment of the present invention, a wearable textile-based harness includes an adjustable elastic horizontal band and an adjustable elastic vertical band. The horizontal band wraps proximate to a body portion around the thoracic cage region and the horizontal band passes over the xyphoid process and thoracic cage between 5th and 6th ribs positions. The vertical band wraps over the shoulder passing between shoulder muscle and deltoid muscle. The vertical band and horizontal band connected in front at the xyphoid process location and at the back on either side of the back-center. A first plurality of sensors are located along a first vector extending along the vertical band on a front side of the harness, wherein the first plurality of sensors include a first and second sensor located along the first vector above the heart of the wearer and a third and fourth sensor located along the first vector below the heart of the wearer, the second sensor being located downward of the first sensor and the fourth sensor located downward of the third sensor. A second plurality of sensors are located along a second vector extending along the horizontal band on the front side of the harness, wherein the second plurality of sensors include a fifth and sixth sensor located along the second vector to the right of the heart of the wearer and a seventh and eighth sensor located along the second vector to the left of the heart of the wearer, the sixth sensor being located downward of the fifth sensor and the eighth sensor located downward of the seventh sensor. Upon wearing the textile-based harness, the first and second plurality of sensors are placed in contact with skin of wearer, preferably with a sensor-skin pressure in the range of 60 to 250 gram-force. The adjustable elastic horizontal and vertical bands may be adjustable via fasteners.

In accordance with other variants of the first embodiment, the elastic horizontal band and the elastic vertical band are made of an elastic fabric, each of the first and second plurality of sensors are located at sensor locations on the elastic fabric, and at one or more of the sensor locations, a non-elastic material is fixed on the elastic fabric, an elastomeric material is fixed on the non-elastic material, and one or more of the sensors is fixed on the elastomeric material.

In accordance with other variants of the first embodiment, the first and second plurality of sensors include at least one textile based nanosensor comprising vertically standing nanofilaments. The sensors may also include a heart sound sensor and/or an IMU.

In accordance with a second embodiment of the present invention, a CHF management system includes a wearable textile-based harness and a signal acquisition unit.

The wearable textile-based harness includes an elastic horizontal band and an elastic vertical band. The horizontal band wraps proximate to a body portion around the thoracic cage region and the horizontal band passes over the xyphoid process and thoracic cage between 5th and 6th ribs positions. The vertical band wraps over the shoulder passing between shoulder muscle and deltoid muscle. The vertical band and horizontal band connected in front at the xyphoid process location and at the back on either side of the back-center. A first plurality of sensors located along a first vector extending along the vertical band on a front side of the harness. A second plurality of sensors located along a second vector extending along the horizontal band on the front side of the harness. Upon wearing the textile-based harness, the first and second plurality of sensors are placed in contact with skin of wearer, preferably with a sensor-skin pressure in the range of 60 to 250 gram-force.

The signal acquisition unit includes an analog front end circuit, a processor, a wireless module, and a power supply, the SAU receiving signals from the plurality of sensors, generating, from the signals, an ECG signal and an ICG signal, and wirelessly transmitting at least the ECG signal and the ICG signal to a remote computing device.

In accordance with other variants of the second embodiment, the harness may include some or all of the features described above with respect to the first embodiment.

In accordance with other variants of the second embodiment, the ECG signal includes a first ECG signal from the first vector and a second ECG signal from the second vector, and the ICG signal includes a first ICG signal from the first vector and a second ICG signal from the second vector.

In accordance with other variants of the second embodiment, the system further comprises the remote computing device, the remote computing device including a processor and computer readable media having stored thereon computer executable process steps operative to control the processor to display on a display screen a graph of the first ECG signal from the first vector as a function of time, a graph of the first ICG signal from the first vector as a function of time, a graph of the second ECG signal from the second vector as a function of time and a graph of the second ICG signal from the second vector as a function of time.

In accordance with other variants of the second embodiment, the first plurality of sensors located along the first vector further comprises a heart sound sensor, wherein the signal acquisition unit further generates a heart sound signal and wirelessly transmits the heart sound signal to the remote computing device, and the remote computing device includes computer executable process steps operative to control the processor to display on a display screen a graph of the heart sound signal as a function of time.

In accordance with a third embodiment of the present invention a method of monitoring cardiovascular health in a human, comprises providing a wearable textile-based harness The harness includes an elastic horizontal band and an elastic vertical band wherein, when worn by the human, the horizontal band wraps proximate to a body portion of the human around the thoracic cage region, the horizontal band passing over the xyphoid process and thoracic cage between 5th and 6th ribs positions, the vertical band wrapping over a shoulder of the human and passing between the shoulder muscle and deltoid muscle, and extending diagonally downward towards the a xyphoid process location, wherein the vertical band and horizontal band are connected in front at the xyphoid process location and at the back on either side of the back-center. A first plurality of sensors located along a first vector extending along the vertical band on a front side of the harness and a second plurality of sensors located along a second vector extending along the horizontal band on the front side of the harness. Upon wearing the textile-based harness, the first and second plurality of sensors are placed in contact with skin of wearer.

The method further includes generating, from the first and second plurality of sensors, at least one ECG vector signal, and at least one ICG vector signal.

In accordance with other variants of the third embodiment, the at least one ECG vector signal includes a first ECG signal from the first vector and a second ECG signal from the second vector, and the at least one ICG vector signal includes a first ICG signal from the first vector and a second ICG signal from the second vector.

In accordance with other variants of the third embodiment, the method further comprises displaying on a display screen a graph of the first ECG signal from the first vector as a function of time, a graph of the first ICG signal from the first vector as a function of time, a graph of the second ECG signal from the second vector as a function of time and a graph of the second ICG signal from the second vector as a function of time.

In accordance with other variants of the third embodiment, the method further comprises generating a plurality of parameters from the ECG and ICG vectors, including: Atrial electrical activity from at least one of the ECG vectors; Ventricular electrical activity from at least one of the ECG vectors; PR interval of atrio-ventricular conduction interval from at least one of the ECG vectors; QRS measures from at least one of the ECG vectors; ST-T measures from at least one of the ECG vectors; Cardiac output from at least one of the ICG vectors; Stroke volume from at least one of the ICG vectors; Cardio-vascular pressures from at least one of the ICG vectors; Pulmonary pressures from at least one of the ICG vectors; Minute ventilation from at least one of the ICG vectors; Shortness of breath from at least one of the ICG vectors; Exercise tolerance from at least one of the ECG and ICG vectors; Heart rate from at least one of the ECG vectors; Heart rhythm from at least one of the ECG vectors; Transthoracic impedance from at least one of the ICG vectors; and Ejection fraction from at least one of the ICG/ECG vectors.

In accordance with other variants of the third embodiment, the method further comprises generating a composite CHF monitoring metric based on data received from the first and second plurality of sensors.

BRIEF DESCRIPTION OF THE DRAWINGS

FIG. 11 shows an exemplary composite data packet for transmitting data from a plurality of channels having different sampling rates.

FIGS. 14(a), 14(b) and 14(c) show an exemplary sequence of user interfaces that the physician would encounter as part of the sequence of steps following to initiate monitoring CHF for a new patient on web portal 602.

DETAILED DESCRIPTION OF THE EMBODIMENTS

Figure 1A:
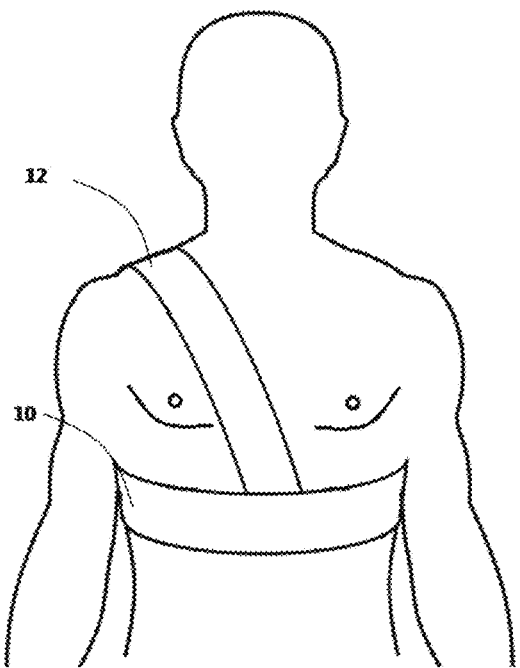
FIGS. 1(a) and 1(b) show a front and rear view of an exemplary wearable textile-based harness model made of an elastomeric fabric material with vertical band attached to one side of the back center.
Figure 1B:
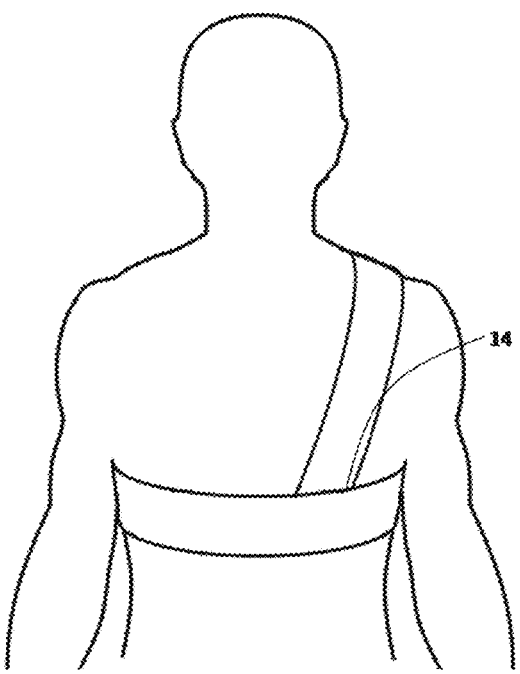
Figure 1C:
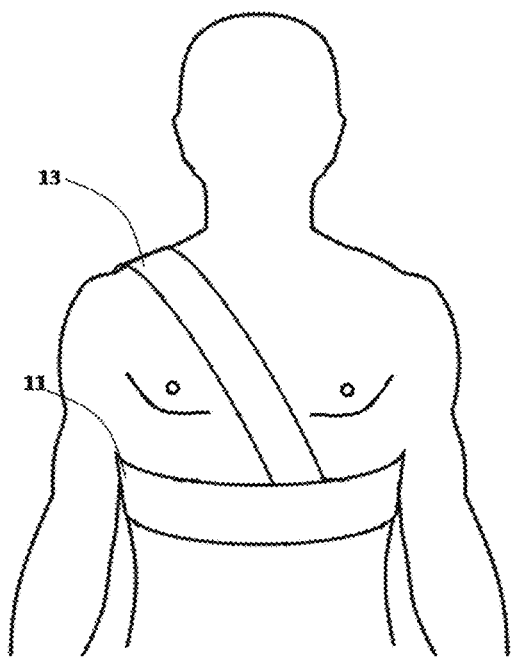
FIGS. 1(c) and 1(d) show a front and rear view of an exemplary wearable textile-based harness model made of an elastomeric fabric material with vertical band attached to the other side of the back center.
Figure 1D:
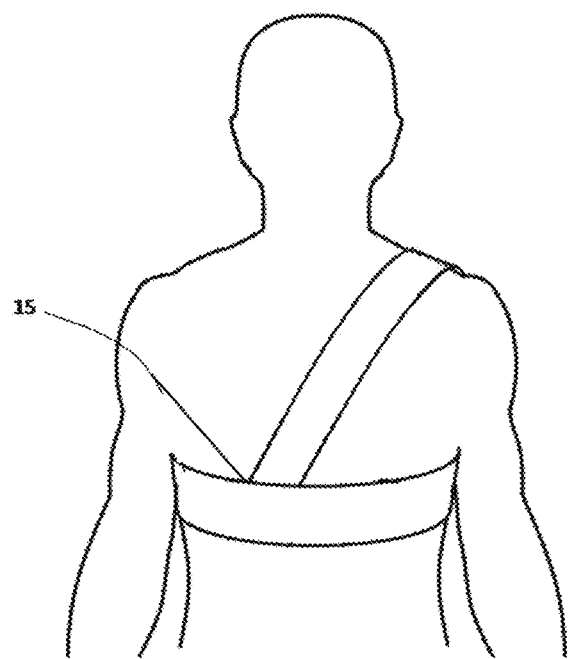

The present invention relates to a non-invasive, wearable and portable medical device for evaluation and monitoring the heart condition for patients with CHF. More particularly, the invention relates to a system including a wearable device utilizing physiologic and biometric sensors, a Signal Acquisition Unit (SAU), and a monitoring system executing a suite of software algorithms to monitor and evaluate patients with Congestive Heart Failure (CHF). More particularly, the system measures physiological parameters including: one or more vectors of ECG, one or more vectors of ICG, impedance (Zo), respiration, heart sounds, and actigraphy and postures.

In particular, the wearable device may be made of an elastomeric harness comprising of active and passive nanosensors, heart sound sensor, an Inertial Measurement Unit (IMU), and a connector to electrically connect the aforementioned sensors to the SAU. The SAU may be comprised of an Analog Front End circuit (AFE), a processing unit, a storage unit, a power supply, and a wireless module.

The monitoring system may include one or more processors executing software that includes a suite of algorithms to monitor, evaluate CHF and heart condition for people already diagnosed with CHF. More particularly, the monitoring system is operable to perform algorithmic parametric extraction of data received from the wearable device from the SAU. The algorithmic parametric extraction includes, but is not limited to, extracting: atrial electrical activity, ventricular electrical activity, ECG rhythm analysis, PR interval or atrio-ventricular conduction interval, patient activity score, posture, cardiac output, stroke volume, relative tidal volume, cardio-vascular pressures, patient geographic location and altitude, pulmonary pressures, minute ventilation, shortness of breath, exercise tolerance, heart rate, transthoracic impedance, and heart sounds. Based on the parametric extraction, a composite CHF monitoring metric is computed by the monitoring system to evaluate and monitor the heart condition and worsening heart failure in CHF patients.

Upon wearing the textile-based harness (wearable device), the sensors present in the harness get placed in specific locations in the body. The sensors acquire raw physiological signals and electrically transmit it to the SAU, which processes the signals and transmit them to the monitoring system for further processing and analysis. When a signal acquisition unit and a smart phone is powered on, the signal acquisition unit and the smart phone are connected to each other wirelessly. A smart phone controls the signal acquisition unit by sending command to the signal acquisition unit through wireless such as Bluetooth, Wi-Fi, or other wireless communication standards. Commands from the smart phone to the acquisition unit include initializing the acquisition unit, requesting to send data to the smart phone for signal quality check at the beginning stage of test, requesting start and stop test, and requesting to upload stored data in the storage of the acquisition unit through wireless after the test is completed. In addition to communicate with the acquisition unit, it sends log symptoms triggered by a patient to the portal or server.

Wearable sensor systems and devices are highly unobtrusive and beneficial for home healthcare monitoring and provide freedom of movement. They are cost-effective, easy to use, compact, non-invasive, and simple yet efficient in operation. Long term monitoring is useful in monitoring chronic diseases like CHF, and the wearable harness truly support non-invasive long-term monitoring. Monitoring, and evaluating patient diagnosed with CHF with one or more of the aforementioned physiological signals and/or derived parameters through a wearable and wireless harness has numerous advantages including: enabling earlier intervention and diagnosis, enable earlier prediction of worsening heart condition, enabling physicians to prescribe better medications, enabling better treatment and therapies to maximize the benefits, avoiding the need for expensive and invasive implantable devices, enabling the wearer to carry on everyday activities, providing freedom of movement, comfortable to wear, replaceable and cost effective, and enabling remote, long-term, continuous and unobtrusive monitoring.

Wearable Device

A wearable textile-based harness, as shown in FIG. 1(a-d), comprises of a horizontal band and a vertical band. FIGS. 1(a-b) show a harness with the vertical band 12 connected to the horizontal band 10 at the front at xyphoid process location and on the back at a location 14 to the right of back center (from the perspective of the wearer). FIGS. 1(c-d) show a harness with the vertical band 13 connected to the horizontal band 11 at the front at xyphoid process location and on the back at a location 15 to the left of back center (from the perspective of the wearer). The harness footprint covers the key sensor positions for measurement of biopotential electrocardiogram (ECG), bioimpedance for impedance cardiography (ICG) and respiration tidal volume and heart sound. The horizontal band covers the horizontal plane of the xyphoid process and is an optimum location for measurement of ventricular heart activity, and lung air intake and lung fluid level. The vertical band covers the region between the mid clavicle position and the 2-3 intercostal space, which is the optimal position for the sensors to detect the atrial heart activity and to measure bioimpedance in combination with sensors placed at the xyphoid process level. The junction point of the horizontal and the vertical band is an optimal location for measurement of S3 heart sound. The sound sensor faces the apex of the heart and can detect S3 sound especially when the patient is in a left decubitus position. The horizontal band 10,11 wraps around the body in the thoracic cage region. The horizontal band passes over xyphoid process and thoracic cage between 5th and 6th ribs positions. The vertical band 12,13 wraps over the shoulder like a satchel passing between shoulder muscle and deltoid muscle. The vertical band is connected to the horizontal band in front at the xyphoid process location and at the back on either side of the back-center 14,15 based on the requirements for compression. The width of the band can be between 1 inch and 6 inches.

Figure 4A:
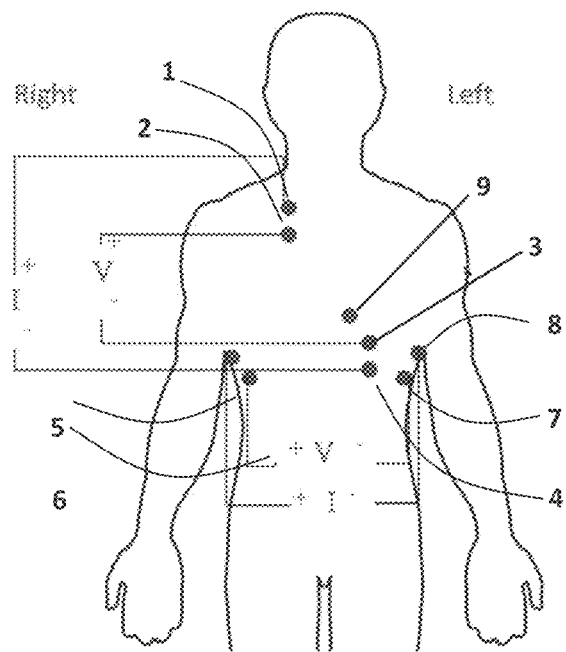
FIGS. 4(a) and 4(b) show exemplary sensor locations along the body and ICG vector configurations for the harness of FIG. 1(a) and FIG. 1(b).
Figure 4B:
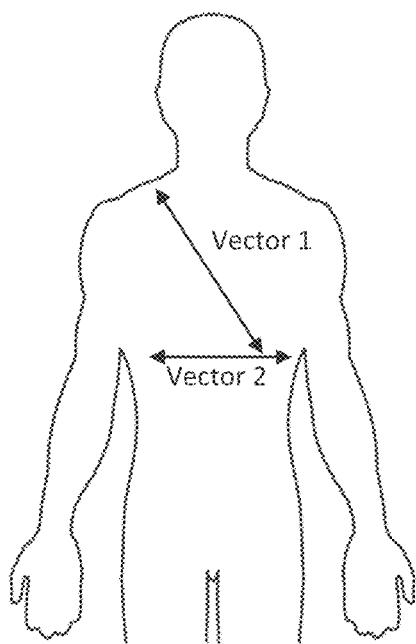

The position of the vertical and horizontal band covers the locations of sensors for detection of ECG signals along the 2 different vectors (see FIG. 4(b) vectors 1 and 2) to capture atrial and ventricular activity. The position also covers sensor locations for capturing hemodynamic activity within the descending aorta as well as the lung filling cycle. The connection point of vertical and horizontal band covers the apex position of the heart to capture S1, S2 and S3 heart sound using a sound sensor.

The horizontal and vertical bands are strapped around the thoracic cage and over the shoulder by using adjustable fasteners such as buckle(s) or Velcro. Preferably, the vertical band is always in a closed position like a shoulder strap, while the horizontal band has open ends. The user fastens the horizontal band around the thoracic cage with the fastener(s) and then slips the vertical band (strap) over the right shoulder. The users can put the harness on and take the harness off by themselves without any help, which enables them to use this device by themselves in the comfort of their home. The size adjustable bands make the harness suitable for users of wide range of sizes and it is gender agnostic. The buckles on the horizontal and vertical bands also allow for adjustment of harness for different size subjects. The elasticity of the harness material allows for the sensors to get placed at the correct position for all size users.

Figure 2A:
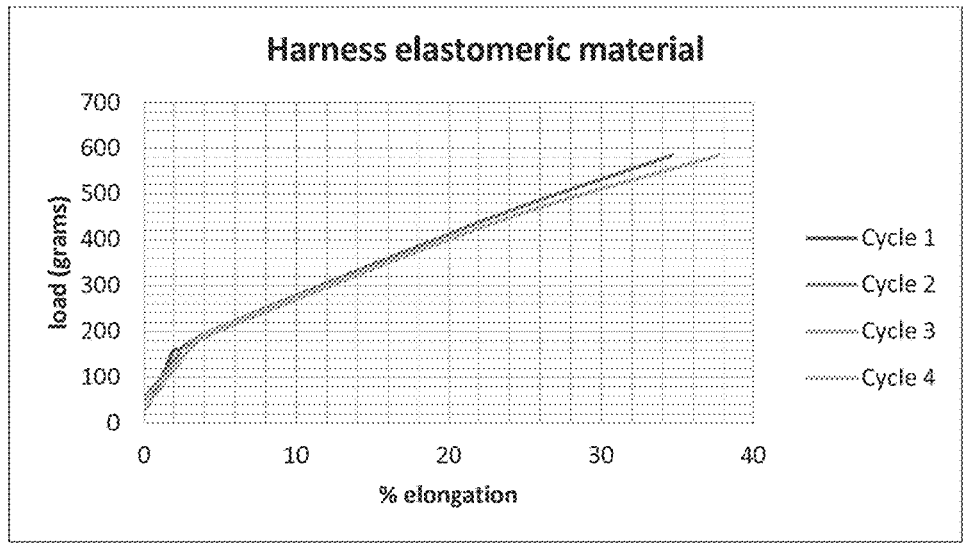
FIG. 2(a) shows a load-elongation curve of the elastomeric material shown in FIG. 1.
Figure 2B:
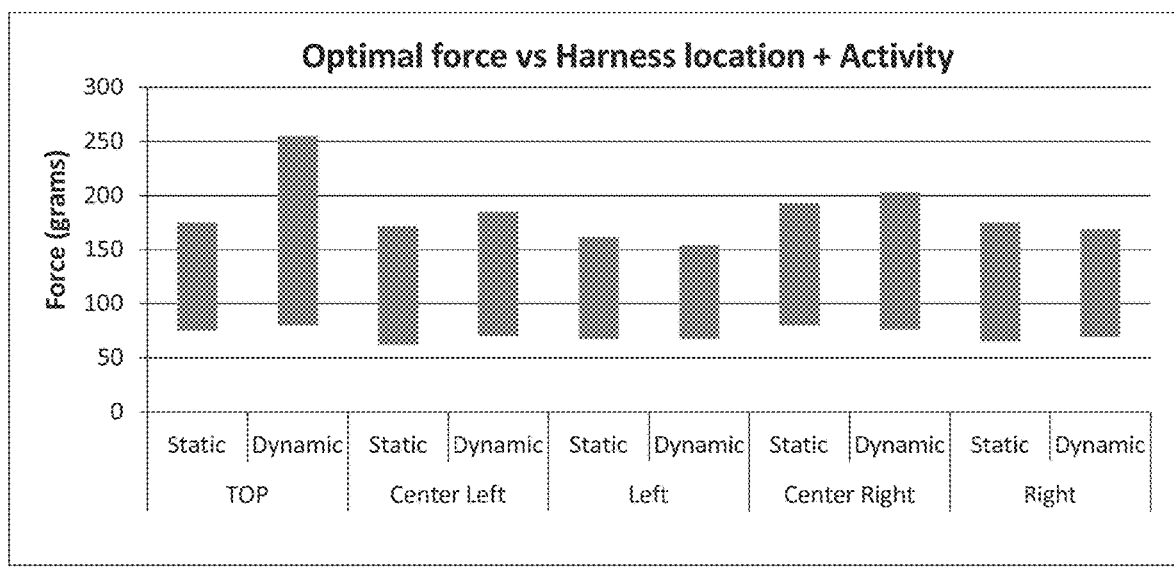
FIG. 2(b) is a graph which shows optimal force vs. harness location based on activity.
Figure 2C:
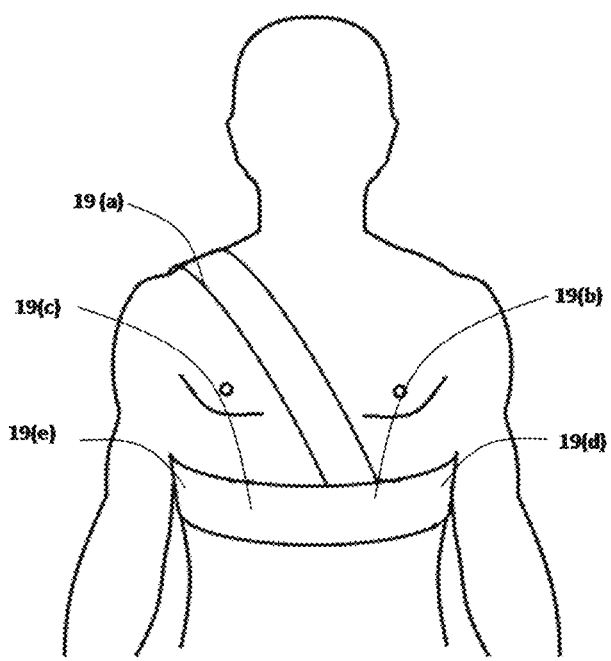
FIG. 2(c) is an illustration of the harness showing five regions.

The bands (10-13) are made of elastomeric compression fabric material that has load-elongation curve for four test cycles as shown in FIG. 2(a). This illustrates that the elastomeric material of the harness maintains its elasticity after repeated loading. The harness design exerts compressive force with the vertical and horizontal bands within a desired force range of 60-250 gf (gram-force) when the user wears the harness in order to effect reliable sensor measurement. FIG. 2(b) shows the compressive force ranges in gram-force at each location of harness during different postures (static) and different movements (dynamic) as shown in FIG. 2(b). As shown in FIG. 2(c), the harness is divided into 5 regions where the sensors are likely to be positioned: TOP 19(a) (on the vertical band), Left center 19(b), Right center 19(c), Left 19(d) and Right 19(e) (all on the front part of horizontal band).

Figure 3A:
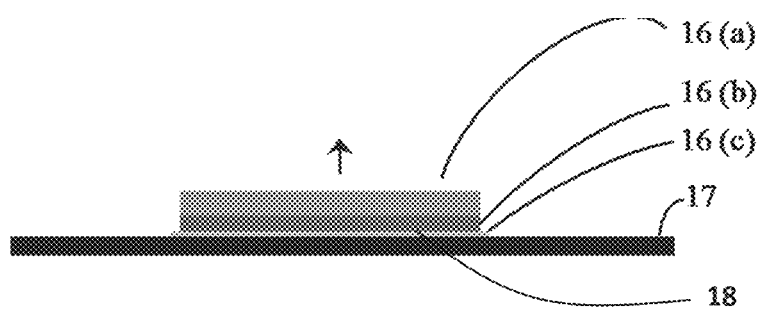
FIGS. 3(a) and (b) illustrate a portion of the harness of FIG. 1(a,b) having a sensor location where the harness is augmented with an elastomeric material and a rigid material to provide protrusion for better skin-sensor contact.
Figure 3B:
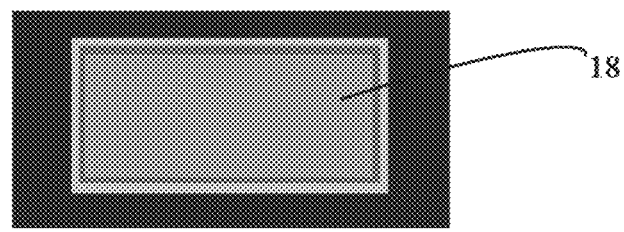

The base fabric 17 of the harness bands is augmented by using elastomeric material 16(b) (shore 00 30-50) at the location 18 for nanosensor(s) 16(a) that rise over the outer surface of the base fabric 17 by 2-6mm as shown in FIG. 3. A non-elastomeric material 16(c), such as a rip stop fabric, is preferably provided between the elastomeric material 16(b) and the base fabric 17, so that that the elastomeric material 16(b) is reinforced with 16(c) to ensure that the configuration 16 does not bulge out toward base fabric 17. The nanosensor 16(a) is attached to 16(b) by thermally cured glues such as polyurethane based adhesive films and silver loaded polyurethane based adhesive pastes. These bonded films are wash resistant. This configuration always pushes out the nanosensors towards the wearer's skin. This implementation is intended for better skin-sensor contact by compensating for different skin contours and hold the sensor in place during movement or change in posture. The elastic fabric may, for example, be polyester with LYCRA/spandex/elastane, nylon with LYCRA/spandex/elastane, cotton poly rib, and the like. The fabric may have a variety of different weaves such as plain, knitted or tricot. The elastomeric material may have a Shore OO hardness of 30-50, and be made of neoprene, EPDM (ethylene propylene diene monomer), polyurethanes, and the like.

The measurement of ECG and ICG is done along 2 different vectors, illustrated in FIG. 4(b). Vector 1 runs diagonally across the rib cage from right shoulder to lower left side of the rib cage. This vector is consistent with Lead II of ECG. Since one of the ECG sensors for this lead is above the heart and the other is below the heart, it can be used for monitoring the atrial activity (P wave) and ventricular activity (QRS complex and T wave). As shown in FIG. 4(a), the set of 4 sensors 1,2,3,4 are placed along vector 1 such that sensors 1 and 2 are above the heart's position and sensor 3 and 4 are placed below the heart's location. Current applied between sensors 1 and 4 passes through the heart and descending aorta to take the path of least resistance and the potential difference is picked up by sensors 2 and 3. Therefore, bioimpedance measured along this vector is affected by the volume of blood being pumped by heart and passing through the descending aorta. It is also affected by the lungs air volume. Accordingly, this bioimpedance signal can be used to derive Impedance Cardiography (ICG) as first derivative of bioimpedance. The respiration signal is the low frequency base line sinusoid in the bioimpedance signal .The relative respiration tidal volume is obtained by measuring the peak amplitude in the respiration signal.

Vector 2 runs across the rib cage from lower right side to lower left side of the rib cage. This vector uses sensors 6 and 7 for measurement of ECG. Since they are placed on either sides of the heart and below the heart, they can pick up ventricular activity (QRS complex and T wave) and in some cases atrial activity (Pwave). The set of 4 sensors 5,6,7,8 are placed such that sensors 5 and 6 are on right side of the heart's position and sensors 7 and 8 are left side of the heat's position. Current applied between sensors 5 and 8 passes through the descending aorta and the thoracic cage space at the lower level to take the path of least resistance and the potential difference is picked up by sensors 6 and 7. Therefore, bioimpedance measured along this vector is significantly affected by the lungs air volume. It is also affected by volume of blood passing through the descending aorta. Accordingly, this bioimpedance signal can be used to derive Impedance Cardiography (ICG) as first derivative of bioimpedance. The respiration signal is the low frequency base line sinusoid in the bioimpedance signal. The relative respiration tidal volume is obtained by measuring the peak amplitude in the respiration signal. Apart from the redundancy provided by this vector, the bioimpedance baseline of this vector is also affected by water retention in the lungs, which is a condition that may be prevalent in Congestive Heart Failure patients.

Figure 5:
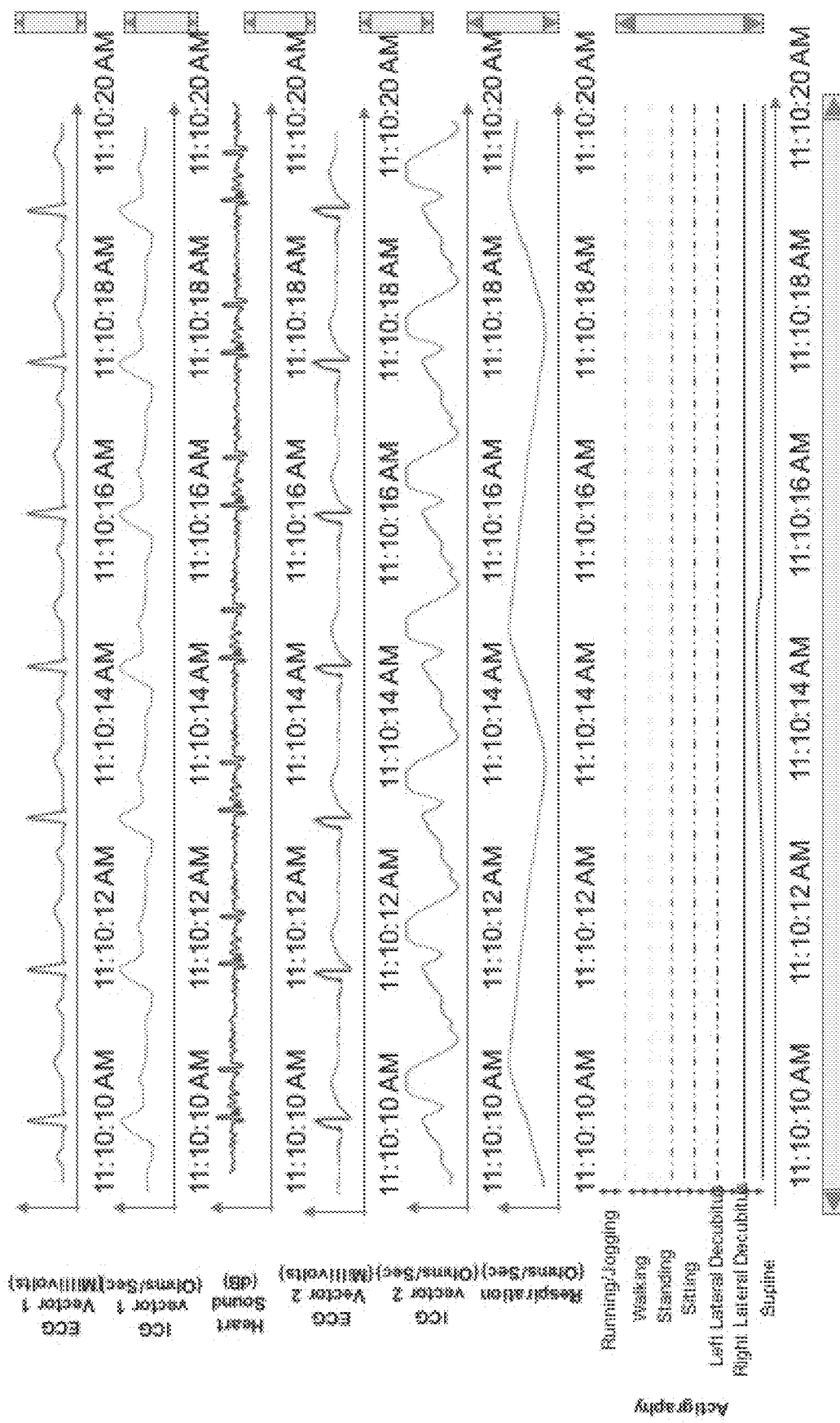
FIG. 5 shows an exemplary data plot showing two vectors of ECG, two vectors of ICG, heart sound, respiration, and actigraphy.
Figure 6:
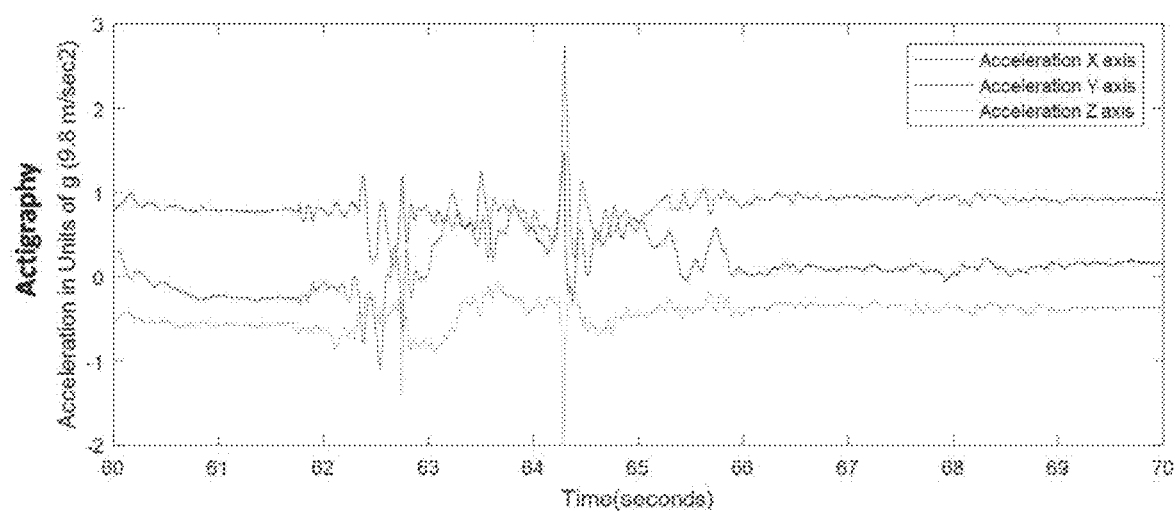
FIG. 6 shows the measured acceleration on three axes for detecting activity and posture.
Figure 7A:
FIG. 7(a) shows a substrate for an exemplary sensor system on a textile based wearable substrate used for detection of ICG, ECG, respiration rate, heart sound and actigraphy.
Figure 7B:
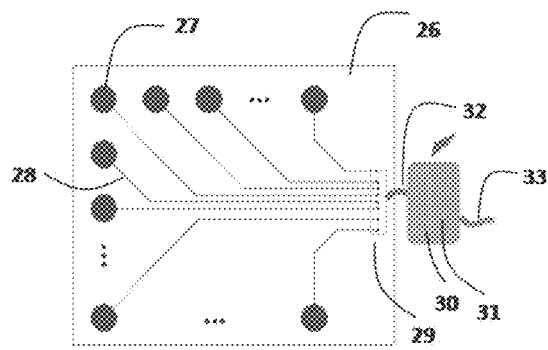
FIG. 7(b) shows circuitry for an exemplary sensor system on a textile based wearable substrate used for detection of ICG, ECG, respiration rate, heart sound and actigraphy.
Figure 7C:
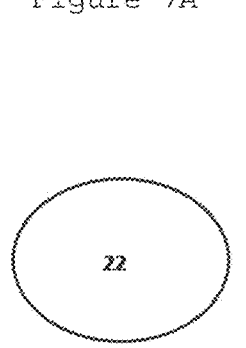
FIG. 7(c) shows an oval shaped substrate for an exemplary sensor system on a textile based wearable substrate used for detection of ICG, ECG, respiration rate, heart sound and actigraphy.
Figure 7D:
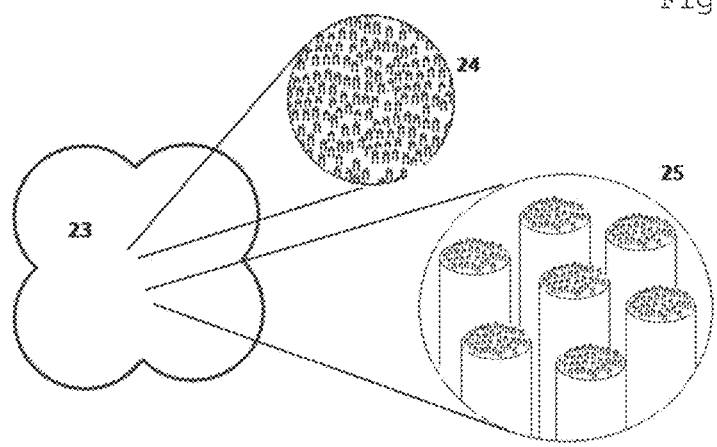
FIG. 7(d) shows a clover-leaf shaped substrate having nanostructures thereon for an exemplary sensor system on a textile based wearable substrate used for detection of ICG, ECG, respiration rate, heart sound and actigraphy

The configuration of sensors as shown in FIG. 4(a,b) give impedance cardiography (ICG) and electrocardiography ECG along vectors 1 and 2 (FIG. 4(b)) with respect to wearer's body. Electrical current (Up to 5 mA) is passed between Nanosensors 1 and 4 (FIG. 4(a)) through the body along vector 1 and Nanosensors 2 and 3 measure change in potential to obtain ICG Vector 1. ECG Vector 1 is the voltage drop (change in potential) across nanosensors 2 and 3 measured passively (e.g., without application of current). Current (Up to 5 mA) is passed between Nanosensors 5 and 8 through the body along vector 2 and Nanosensors 6 and 7 measure change in potential to obtain ICG Vector 2. ECG Vector 2 is the voltage drop (change in potential) across nanosensors 6 and 7 measured passively (e.g., without application of current). Current is applied as a modulated signal, such as a square wave, and the corresponding change in potential is measured by nanosensors and impedance Z0 is calculated for ICG. The same nanosensors 2,3,6,7, measuring change in potential, also passively measure ECG along the respective vector (e.g. without the application of current). The measured impedance (Z0) is processed to extract respiration rate. The first derivative of impedance (Z0) gives the dZ/dt. The dZ/dt is presented as ICG and respiration is extracted from Z0 as shown in FIG. 5. The respiration signal is the low frequency base line sinusoid in the bioimpedance signal (Z0). The relative respiration tidal volume (discussed below) is obtained by measuring the peak amplitude in the respiration signal. The ECG and ICG from vectors 1 and 2 are shown in rows 1,2 and 4,5 respectively. Respiration, in row 6, is derived from vector 2 ICG. The activity data in row 7 of FIG. 5 is derived from signals from inertial measurement unit (IMU) data shown in FIG. 6.

A heart sound signal is shown in row 3 of FIG. 5. A heart sound sensor system 9 is used in the detection of heart sound. This heart sound sensor can either be a MEMS, piezoelectric, condenser and acoustic microphone, or accelerometer-based sensing element. The heart sound sensor is packaged in a moisture and dust proof flexible enclosure, so that it can be protected from body sweat and dead skin and, so that it can withstand wash cycles. It is positioned such that it is oriented towards the lower apex of the heart. The heart sound sensor is preferably mounted on a sound absorbent material such as neoprene rubber foam with micro air-cavities. The foam mount has void space to house the heart sound sensor. An inertial measurement unite (IMU) is mounted on the harness at or near the same location as heart sound sensor. The IMU measures linear acceleration, angular rotation, and magnetic field vectors to detect movement and rotation shown in FIG. 6. It also tracks the orientation of the wearer's body. IMU's are commercially available from a variety of manufacturers, including but not limited to Analog Devices Inc, Microchip Technology, Honeywell Sensing and Productivity Solutions, Maxim Integrated, TDK Invensense, etc.

FIG. 7(*a-d*) shows a diagram of a sensor system on a textile based wearable substrate used for detection of ICG, ECG, respiration rate, heart sound and actigraphy. The substrate 20, 21 (FIG. 7(*a*)) can be a wearable form factor such as patch, harness or garment. In the context of FIG. 1, the horizontal band 10/11 and vertical band 12/13 are made of the substrate 20/21, with sensors on side 20 facing the skin. In other words, in the context of FIG. 3, the substrate 20/21 corresponds to elastic fabric 17. Alternatively, the substrate 20/21 could be glued, sewed, or otherwise secured to the bands 10/11, and 12/13. The sensor system is comprised of one or more nanosensors, heart sound sensor and IMU on the side 20 in contact with wearer's skin. The sensor shapes/patterns may be circular, oval 22 (FIG. 7(*c*)), clover leaf 23 (FIG. 7(*d*)) or fractal carpet of sensors which are connected in different configurations to optimize signal detection. Such shapes can be used to achieve better contact on contoured interface such as fabric touching the human body. As one or ordinary skill in the art will appreciate, a fractal carpet is array of sensors arranged in a repeated geometric pattern, where the individual sensors can be of any shape (circle, square etc.).

Preferably, side 20 also incorporates the conductive tracks 27, 28 and connectors 29 (FIG. 7(*b*)). Accordingly, in the context of FIG. 3, conductive tracks are on skin-facing side of fabric 17, and are connected through layers 16(*b*) and 16(*c*) to sensor 16(*a*) having nanosensors 22/23. Nanosensors 22 or 23 are printed nanosensors that are used in sensing ICG, ECG and respiration signals. The nanosensor surface has vertically standing nanofilaments that form a uniform coverage 24 on the sensor surface or form hierarchical structures 25 (FIG. 7(*d*)). One or more nanosensors 22 or 23 are printed and/or bonded onto the substrate 20 in an array. Conductive tracks 27, 28 are printed in or on the fabric 26, and are used to relay the sensed signal from the sensor to electronics 31 through a connector 29. The connection between the fabric and electronics can be established by directly attaching the connector 29 and a connector 30 together or through conductive wires 32. Signals are received in electronics 31 and are processed and stored or transmitted wirelessly to a receiver or cloud network for remote monitoring. The electronics 31 can also be connected to computing equipment via cables 33 to monitor or analyze the signals.

The nanosensors are textile-based sensors. Two/three component yarn, which has polymer nanofibers embedded in a matrix of another polymer, can be used in fabrication of the nanosensor 22,23. Embedded nanofibers can be released by dissolving the matrix polymer. Vertically standing nanofilaments on fabric can be obtained by electrostatic or pneumatic deposition of two/three component fibers followed by dissolving the matrix polymer. The two/three component fibers have static charge that is imparted to them by chemical treatment of the fiber surface. These fibers respond to externally applied electrostatic field. The externally applied static field drives the fibers to adhesive coated textile substrate and makes them stand upright. The deposition is site specific because it is defined by the pattern of adhesive printed on fabric 20 that helps fibers adhere to fabric surface. The matrix polymer is then dissolved to expose the embedded nanofilaments. These nanofilaments are coated with conductive material to make them nanosensors.

The deposition and coating processes can be done in two ways: a) with nanostructured fibers not coated with conductive material are deposited on the textile substrate and coated with conductive material later, for example, by an electroless plating process or b) with nanostructured fibers pre-coated with conductive material such as silver, gold, platinum, polyaniline, polypyrrole, poly(3,4-ethylenedioxythiophene) and rendered conductive and depositing these fibers on the textile substrate. For example, precoated nanostructured filaments can be prepared prior to the deposition process by batch spray coating the filaments, or by coating vertically freestanding nanostructured filaments on a dissolvable substrate followed by release of the vertically freestanding nanofilaments by dissolving the substrate.

The nanosensors and methods for manufacturing the same are described in further detail in US 2018/0080126, 2017/0226643, and 2016/0222539, each entitled Large Scale Manufacturing of Hybrid Nanostructured Textile Sensors, US 2013/0211208, entitled Smart Materials, Dry Textile Sensors, and Electronics Integration in Clothing, Bed Sheets, and Pillow Cases for Neurological, Cardiac and/or Pulmonary Monitoring, US 2017/0225447, entitled Roll-To-Roll Large Scale Manufacturing and Electronics Integration Process of Wireless Nanosensor Systems for Human Health Monitoring, US 20130281815, and US 2013/0281795, each entitled Wearable Remote Electrophysiological Monitoring System, the entire disclosures of which are hereby incorporated by reference in their entirety.

Electronics

Figure 8:
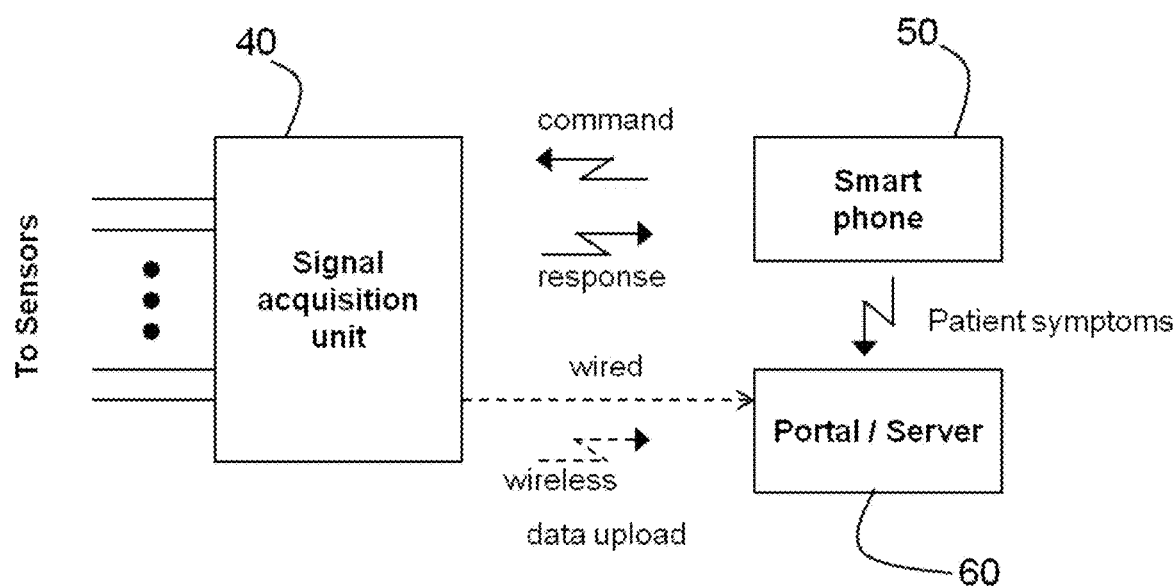
FIG. 8 illustrates an exemplary data flow of the CHF management system.

FIG. 8 illustrates data flow of the CHF management system. When a signal acquisition unit 40 and a smart phone 50 is powered on, the signal acquisition unit and the smart phone are connected to each other wirelessly. The smart phone controls the signal acquisition unit by sending command to the signal acquisition unit wirelessly such as Bluetooth, Wi-Fi, or other wireless communication standards. Commands from the smart phone to the acquisition unit include initializing the acquisition unit, requesting to send data to the smart phone for signal quality check at the beginning stage of test, requesting start and stop test, and requesting to upload stored data in the storage of the acquisition unit wirelessly after the test is completed. In addition to communicating with the acquisition unit, the smart phone 50 it sends log symptoms triggered by a patient to the portal or server. Once the test is started, the signal acquisition unit acquires and processes signals from sensors. The processed signals are stored to the storage such as a SD card or flash memory. Once the test is completed, the stored data are transferred and uploaded to the server or the portal 60 through wired connection or wireless connection.

Figure 9:
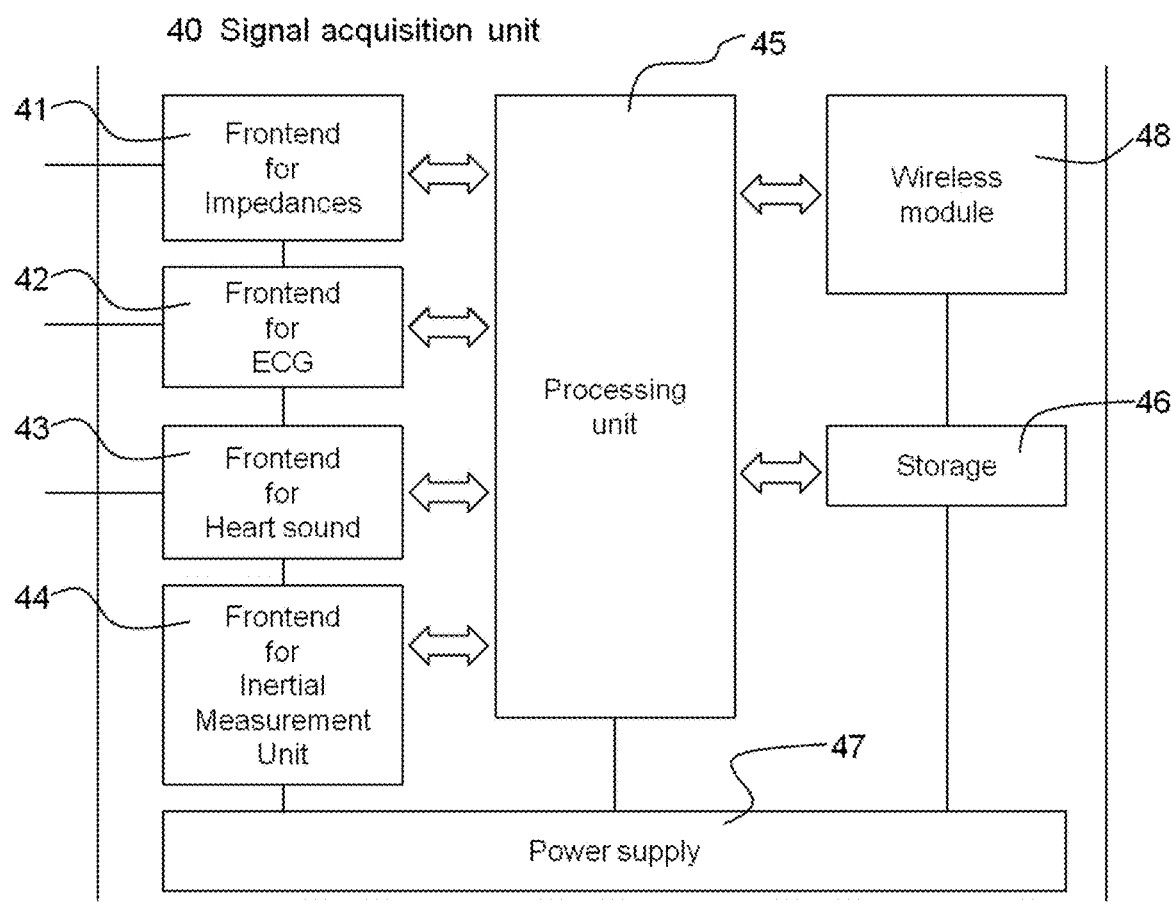
FIG. 9 is an exemplary block diagram for the SAU.

FIG. 9 illustrates a block diagram of the signal acquisition unit 40. The signal acquisition unit (SAU) is designed to be suitable for integration into the harness. Although this is preferred, the SAU could also be located separately or on a different garment. An Analog Front End circuit for impedances 41 can have multiple modulation and demodulation circuits to measure multiple impedance vectors. An Analog Front End circuit for ECGs 42 can have multiple amplifier and filter circuits to measure multiple ECG signals. An Analog Front End circuit for Heart sound 43 can also have multiple amplifier and filter circuits to sense the multiple heart sounds and use them to signal processing such as noise cancellation. The front-end circuit for impedance 41, the front-end circuit for ECGs 42, the front-end circuit for heart sound 43, and the front-end circuit for IMU are connected to the processing unit 45 (e.g. a microprocessor) to allow processing of the signals. The front-end circuit for IMU 44 detects a patient's posture and activity. This front-end includes amplifiers and filters to process the signals from IMU. The processed signals are used to detect patients posture and activity. The IMU may also be used for compensation of the signals affected by the patient's movements. A power supply 47 is to provide the proper voltages and power to each circuit from a battery to power up the acquisition unit 40.

Such Analog Front End circuits, which include amplifiers, filters, and associated circuitry for converting analog sensor signals into digital signals which can processed by a microprocessor are well known in the art and are commercially available from a variety of sources, including Texas Instruments, Microchip Technology, Samsung Semiconductor, Panasonic Electronics Components, STMicroelectronics, Microsemi Corporation, NXP USA Inc, Analog Devices, etc.

The SAU 40 also includes a memory or local storage medium 46 for storing the code or software for operating the microprocessor 45 and for storing data, including data received from the sensors.

The SAU 40 also includes a wireless module for effecting wireless communication with the smart phone 50 and web server 60 via Bluetooth, Wi-Fi, or other wireless communication standards. Such wireless modules are well known in the art and are commercially available from a variety of sources, including Texas Instruments, Microchip Technology, Samsung Semiconductor, Panasonic Electronics Components, Abracon LLC, Murata Electronics North America, etc.

Software

The SAU 40 has a storage medium 45 that contains microprocessor or microcontroller executable code 401 that performs the steps of capturing and converting the signals from the sensors and IMU into machine readable digitized data. The code 401 also creates arrays of digitized data that are stored in a traditional file system for subsequent retrieval in local storage medium 46. This storage medium is non-volatile memory that can be erased and programmed as needed. The code 401 also transmits and receives data and commands to and from an internet connected database service that resides in a remote physical database server such as web server 60, and to and from smart phone 50, through wireless module 48. The code 401 can communicate with the server directly and transfer the acquired data for a patient if a smart phone 50 is not within wireless communication range of the signal acquisition unit 40.

Figure 10A:
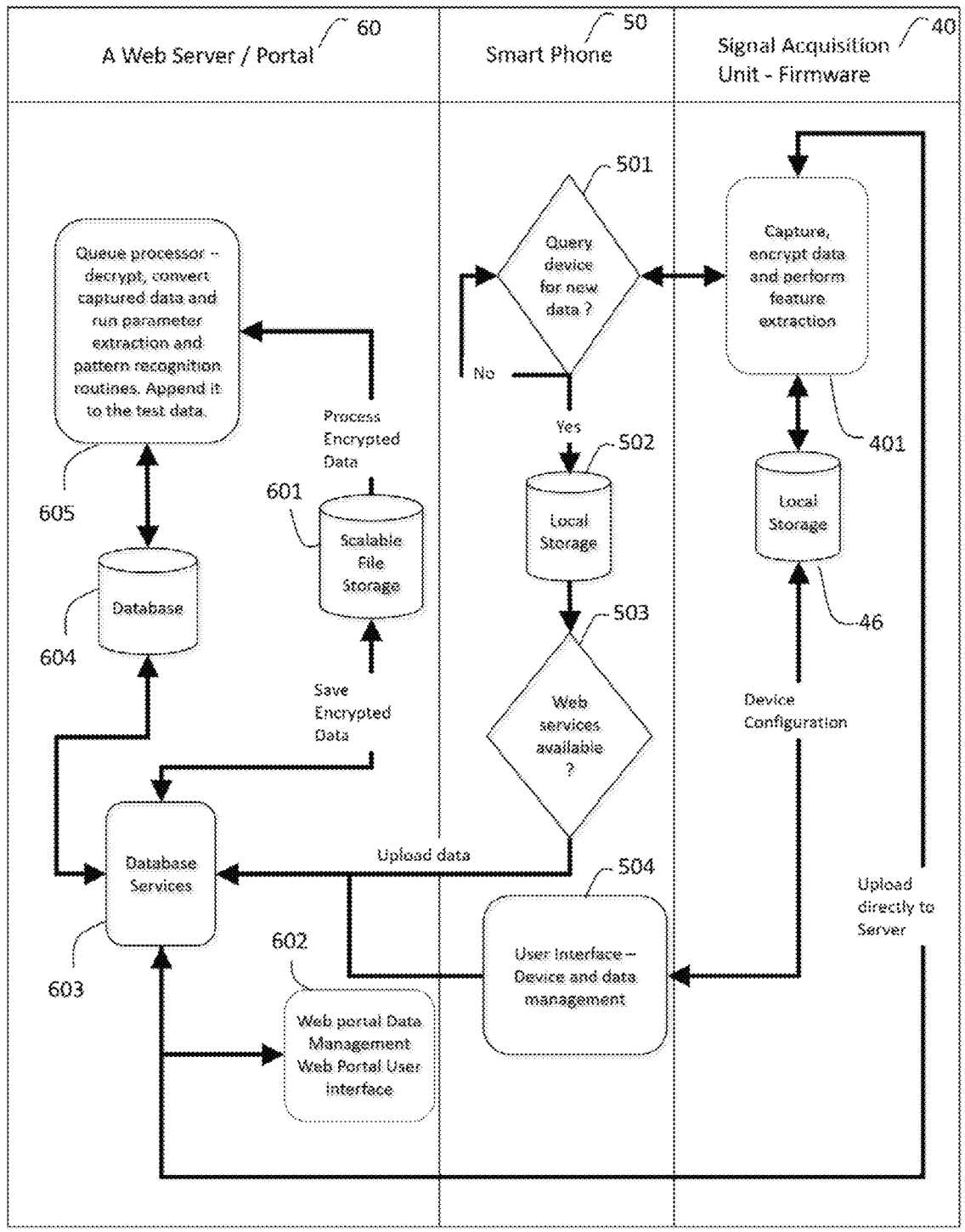
FIG. 10(a)-(b) are flow charts which illustrate the operation of the various software modules that make up the Web services that manage and present the data in a user interface.
Figure 10B:
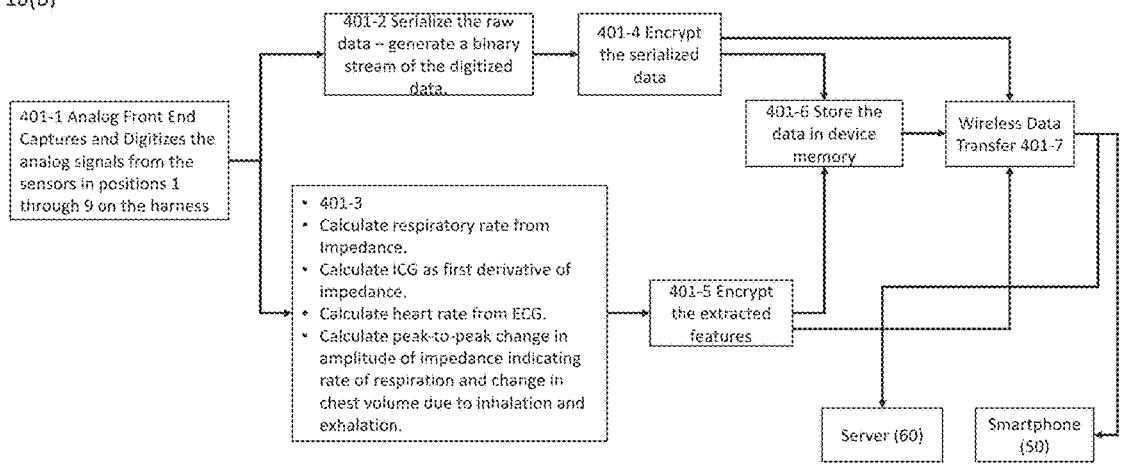

FIGS. 10(a) and 10(b) show illustrative steps of code 401, in further detail.

Code 401 preferably captures and digitizes data from several channels that can have different sampling frequency requirements (step 401-1). In this regard, the code 401 can serialize the digitized data and generate packets on a per second basis or at a frequency equivalent to the lowest sampling frequency (step 401-2 and 401-3). An exemplary implementation of serialization for a set of signals sampled at different frequencies is provided in FIG. 11. The lowest sampling rate here is 50 Hz. Therefore, a composite packet as described in Figure is generated every 20 milliseconds, encrypted and stored in the SAU.

Code 401 also performs feature extraction including: calculate respiratory rate from impedance Z0, calculate ICG as first derivative of impedance Z0, calculate heart rate from ECG, calculate peak-to-peak change in amplitude of impedance indicating rate of respiration and change in chest volume due to inhalation (step 401-3). These extracted features are then encrypted (401-5) and stored (401-6) in memory 46, for later transmission to the smart phone 50 and/or web server 60 (401-7). It should be noted that although the feature extraction is preferably performed on the SAU 40, it is also possible to instead perform these steps on smart phone 50 or web server 60.

The smart phone 50 includes a microcontroller or microprocessor and a storage medium that contains microcontroller or microprocessor executable code 501. FIGS. 10(a) show illustrative steps for the code 501. The code 501 can perform the functions related to the command and interface functions in FIG. 8. The command responses may include but not limited to the following list of commands and their associated responses and descriptions.

TABLE 1

| Command Name | Command code(HEX) | Command Description |
| --- | --- | --- |
| ACC_FileDuration | 0x00 | This command is used to set the amount of data to be stored in a single file. |
| ACC_StatusVariable | 0x01 | This command is used to query the module for its current status. |
| ACC_StartAcquisitionRequest | 0x02 | This command will start the signal data acquisition from the Analog front End. The acquired data is encrypted and stored on the SD card. |
| ACC_RealTimeClockSet | 0x03 | This command is used to set the Real Time Clock and Calendar values on the Microcontroller. This operation needs to be done to synchronize the time between the smart device 20 and the time included in the data files that are captured by 10. |
| ACC_FileTransferRequest | 0x04 | This command is used to request completed files from the module. The module will search for the requested file and start transferring the contents of the file from the Signal acquisition unit |
| ACC_RealTimeReadRequest | 0x05 | This command returns the value of the Real-time clock and calendar on the SAU 10. |
| ACC_StopAcquisitionSleep | 0x06 | This command instructs the module to go to sleep mode where all functions of the SAU are suspended. |
| ACC_RealTimeStreamRequest* | 0x07 | Streams the acquired data to the smart device in a specified format |
| ACC_SetEncryptionKey | 0x08 | This command is used to set the encryption key on the SAU at the beginning of the test. |
| ACC_CurrentFileNumber | 0x09 | This command is used to query the module to determine the current file number. |
| ACC_DeviceID | 0x0A | This command is read the device ID information |
| ACC_FileSize | 0x0B | This command is used to determine the number of bytes in each file. |
| ACC_FileTransferCancel | 0x0C | This command is used to cancel an ongoing file transfer. |
| ACC_SendKeepAlive | 0x0D | This command is used to request the SAU to send message beacons that serve as pings to keep the smart device app active. |
| ACC_DataSession | 0x0E | This command is used by the Smart device to inform the SAU that a data connection is either started or is about to terminate. |
| ACC_GetGPSlocation | 0x0F | This command is used by the SAU to inquire the smart device and retrieve GPS location including altitude from a GPS service on the smart device. |

Using the commands above, the code 501 sends and retrieves data from the SAU 40. The commands above were created following a standard programming design pattern known as command pattern known to those skilled in the art.

The code 501 also stores and accesses data on the local storage 502 in the smart phone 502, including, for example, storing data received from the SAU. Code 501 can further communicate with the operating system code 503 in smart phone 50 regarding the availability of an internet connection that will allow communication to web services, and codes 501, 503 effect uploading of data to the web server 60. The code in 501 further communicates with a user interface and data managing software module 504. The interfaces between the patient or end user and the smart phone are implemented by this module.

The Web server/portal 60 is implemented as 2 services that work in tandem, in an asynchronous manner. The web server 60 includes one or more processors, memory, and software code as described below. The data base services code 603 are responsible for collecting the data acquired by the SAU, received either directly from the SAU 401 or through the smart phone software code 501, 503. The database services code 603 route the data to a secure cloud storage database 601 that is capable of auto-scaling to meet increased demands as needed. As soon as new data files are available in database 601, queue processor code 605 process the data files. Queue processor code 605 may include, but is not limited to performing the following steps:

1. DecrypT the encrypted data from database 601 into unencrypted data.
2. Parse of the unencrypted (raw) data to separate them into individual channels of physiological data;
3. perform any needed data type and format conversions to allow for further processing, including converting digitized recordings into physical values such as voltage and impedance.
4. perform calculation, extraction, and pattern recognition to effect the determination of parameters/features listed in the following table:

TABLE 2

| Name of Parameter/feature | Derivation of parameter/feature | Signal from which parameter is extracted/computed | Significance/ Conclusion |
| --- | --- | --- | --- |
| Atrial Electrical Activity | Duration and amplitude of P wave of ECG waveform | ECG vector(s), | Indicative of anomalies if present in the atrial chambers of the heart |

TABLE 2-continued

| Name of Parameter/feature | Derivation of parameter/feature | Signal from which parameter is extracted/computed | Significance/ Conclusion |
|---|---|---|---|
| Ventricular Electrical Activity | Duration and amplitude of QRS wave of ECG waveform | ECG vector(s) | Indicative of anomalies if present in the ventricular chambers of the heart |
| PR interval or Atrio-ventricular conduction interval | Time elapsed between P wave and R wave occurrence in an ECG | ECG vector(s) | Time taken for atrial impulse to reach the ventricle |
| QRS measures | Amplitude, duration and axis of QRS waves of ECG. | ECG vector(s) | Indicative of anomalies if present in the ventricular chambers of the heart |
| ST-T wave measures | ST segment amplitude, duration and slope in ECG waveform | ECG vector(s) | Indicative of anomalies if present in the relaxation of heart muscles after a beat |
| Patient Activity Score | Measure of physical activity performed by patient like walking, climbing stairs or more intense exercise | Actigraphy - pattern of changes in acceleration from a 3-axis accelerometer, from IMU | Indicative of willingness to be active. |
| Posture | Measure of the absolute posture maintained | Actigraphy - IMU has a 3-axis accelerometer that provides orientation with respect to gravity. | a preference for reclined instead of supine is indicative of fluid accumulation in the lungs. |
| Cardiac Output | Measure of the volume of blood pumped from the heart in a minute. It is the product of the volume of blood pumped out be the left ventricle of the heart and the heart rate. | ICG vector(s) - Product of Area under the curve of ICG waveform following the occurrence of a R peak in the simultaneously acquired ECG, and heart rate as 60 times the inverse of time interval between R peaks in the ECG waveform. | Measure of the heart's pumping efficiency |
| Stroke Volume | Measure of volume of heart pumped from the ventricle of the heart. | ICG vector(s) - Area under the curve of ICG waveform following the occurrence of a R peak in the simultaneously acquired ECG. | Measure of the heart's pumping efficiency |
| Cardio-vascular Pressures | Measure of the maximum pressure in the blood vessels following a heart muscle contraction that causes blood flow and pressure between consecutive contractions. | ICG vector(s) - Slope of the peak following cardiac contraction is inversely proportional to the blood flow pulse velocity, which is proportional to vascular pressure. | Indicative of the health of the vascular system and risk factors such as chronic hypertension. |
| Patient Geographic Location and Altitude | Global Positioning Satellite (GPS) location of the patient from the patient's smart device. | Acquired from SmartDevice using a command-response interface - A GPS module is present in all smartdevices. This module can be interrogated to get current location and altitude. | Indicates whether patient is exposed to high altitude conditions, or travel. |
| Pulmonary Measures | Pulmonary measures include tidal volume - volume of air inhaled or exhaled during normal breathing, and rate of breathing, whether the patient is experiencing shortness of breath wherein the respiratory rate is high, but the volume of air displaced from the lungs is low. | ICG vector(s) - The low frequency baseline variation of impedance is extracted as respiratory signal using filters such as a median filter. Impedance increases with inhalation and lowers with exhalation. | Indicative of the lung function of the patient and whether the patient is experiencing shortness of breath. |

TABLE 2-continued

| Name of Parameter/feature | Derivation of parameter/feature | Signal from which parameter is extracted/computed | Significance/ Conclusion |
|---|---|---|---|
| Minute Ventilation | Measure of the amount of air displaced by the lungs in a minute. | ICG vector(s) - It is the product of the tidal volume from pulmonary measures and the respiratory rate. | Indicative of the lung function of the patient and whether the patient is experiencing shortness of breath. |
| Shortness of Breath | Measure of the amount of air inhaled or exhaled and rate of respiration. | ICG vector(s) - from calculation of minute volume and respiratory rate. | Shortness of breath is a direct indication of worsening heart failure leading to hospitalization. |
| Exercise Tolerance | Measures the changes in heart rate and respiration while performing activities like a 6-minute walk | ECG and ICG vector(s) - heart rate and respiration are derived from the inverse of the RR intervals from ECG, and median filtered impedance curve. | Lowering of exercise tolerance is a leading indicator of worsening heart failure. |
| Heart Rate | Measures the total number of heart beats per minute | ECG vector(s) - Derived as number of R peaks present within a one-minute time window | Elevated heart rate suggests that the heart is unable to output sufficient volume of blood during a single cardiac cycle |
| Heart Rhythm | Measures the regularity of the heartbeat. | ECG vector(s) | Irregular heart beat indicates that there are underlying abnormalities with the electrical activity of the heart. |
| Transthoracic impedance | Measures the electrical impedance of the thorax or chest of the patient. | ICG vector(s) | Thoracic impedance will be lower in patients with fluid accumulation. This is a predictor of impending hospital admission due to shortness of breath. |

5. Perform pattern recognition tasks on any features extracted by the step 4 above to generate conclusions on the patient or end users current CHF burden, prognosis and treatment recommendations. Examples of such conclusions are set forth in Table 2.

Queue processor code 605 can further send an email to the appropriate physician based on any anomalies detected in the measured data such as deviations from thresholds that are set by the physician for each parameter that is monitored in a CHF patient.

After the data files have been processed by code 605, the resulting meta-data, features or parameters are stored in a database 604. The databases 601 and 604 may be combined in a single database in a manner that is known to any person skilled in database management systems.

The web portal front end 602 is responsible for the management of the processed data and generating a user interface wherein the data is presented in a human readable form to a physician. Front end code 602 accesses the data that has been processed by code 605 through the database services in code 603.

Figure 12:
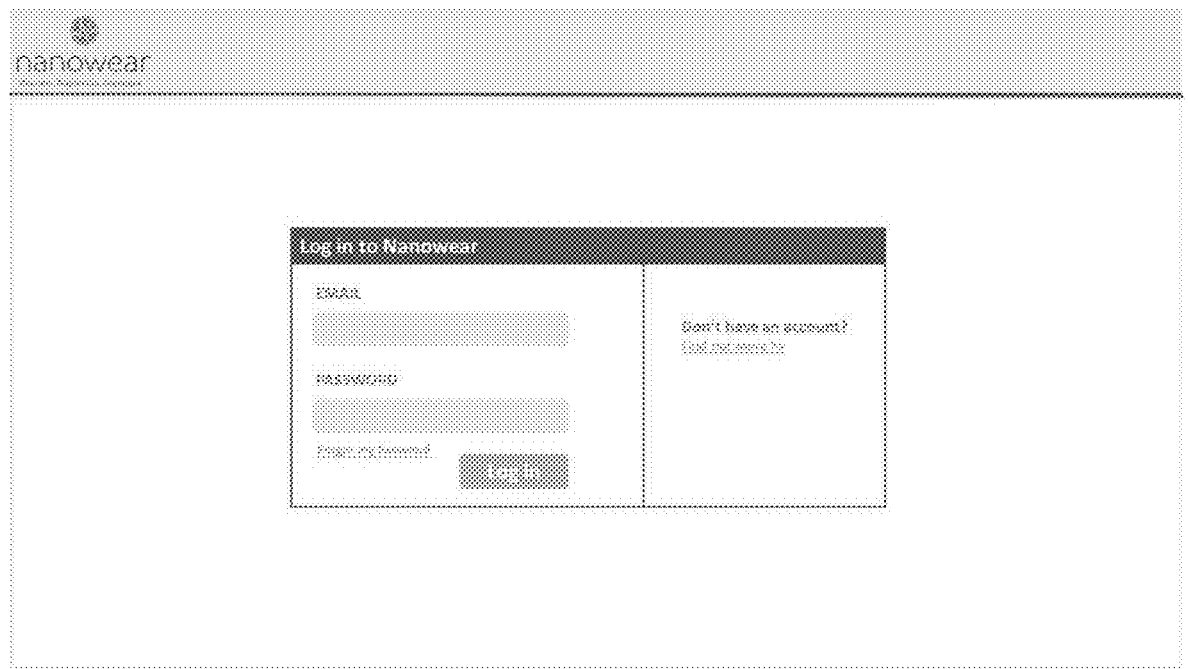
FIG. 12 shows an exemplary login page for a physician on the web portal 602.
Figure 13:
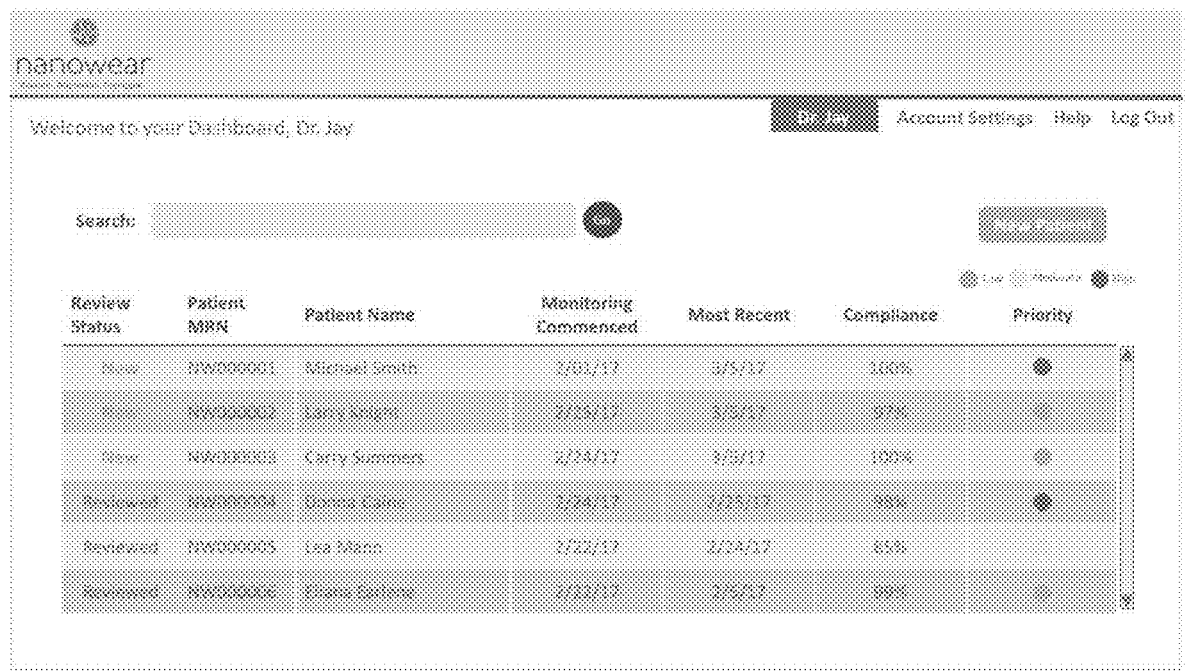
FIG. 13 shows an exemplary landing page for the physician on web portal 602.
Figure 14A:
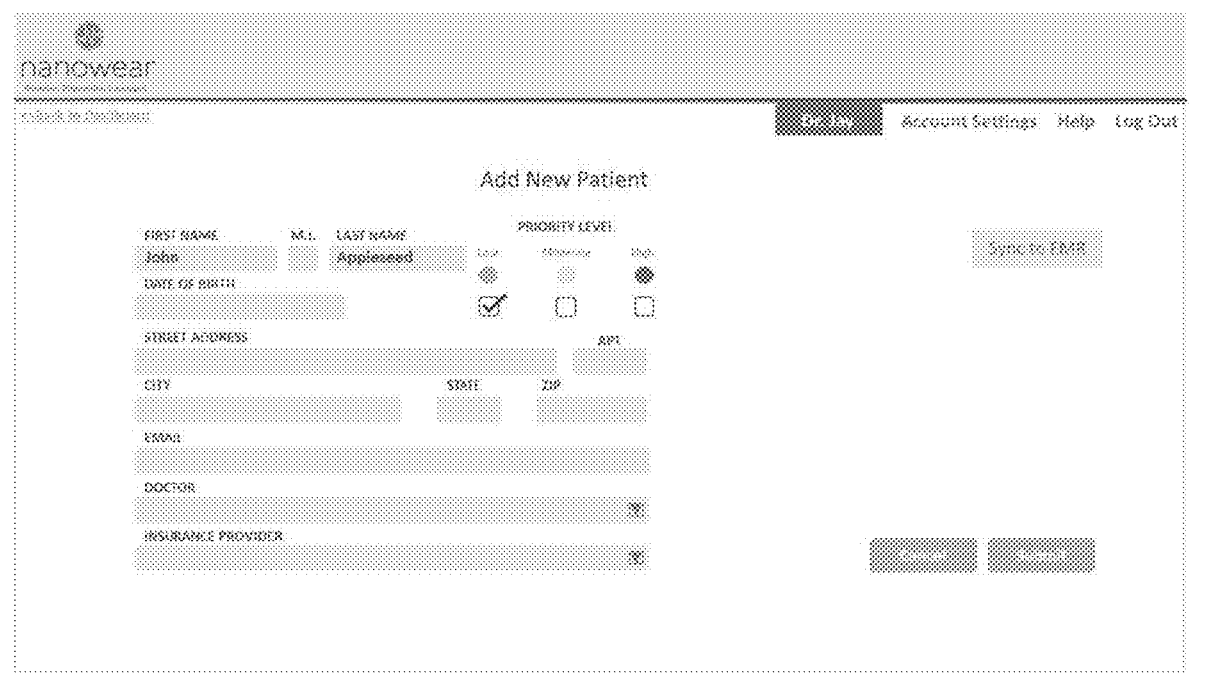
Figure 14B:
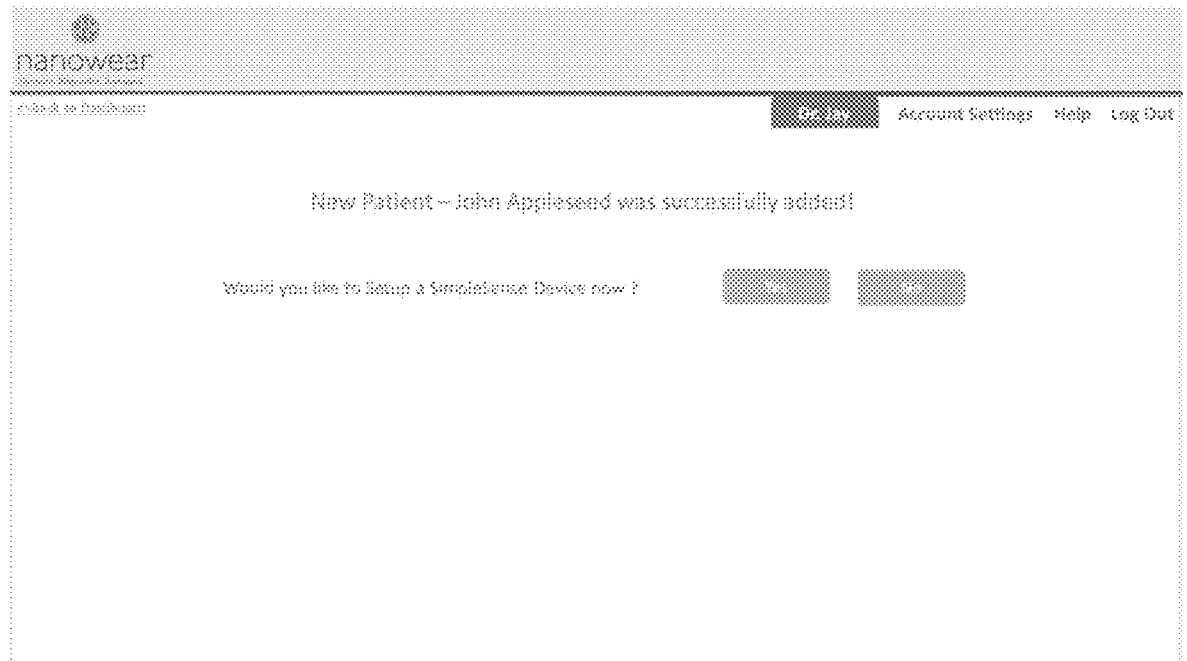
Figure 14C:
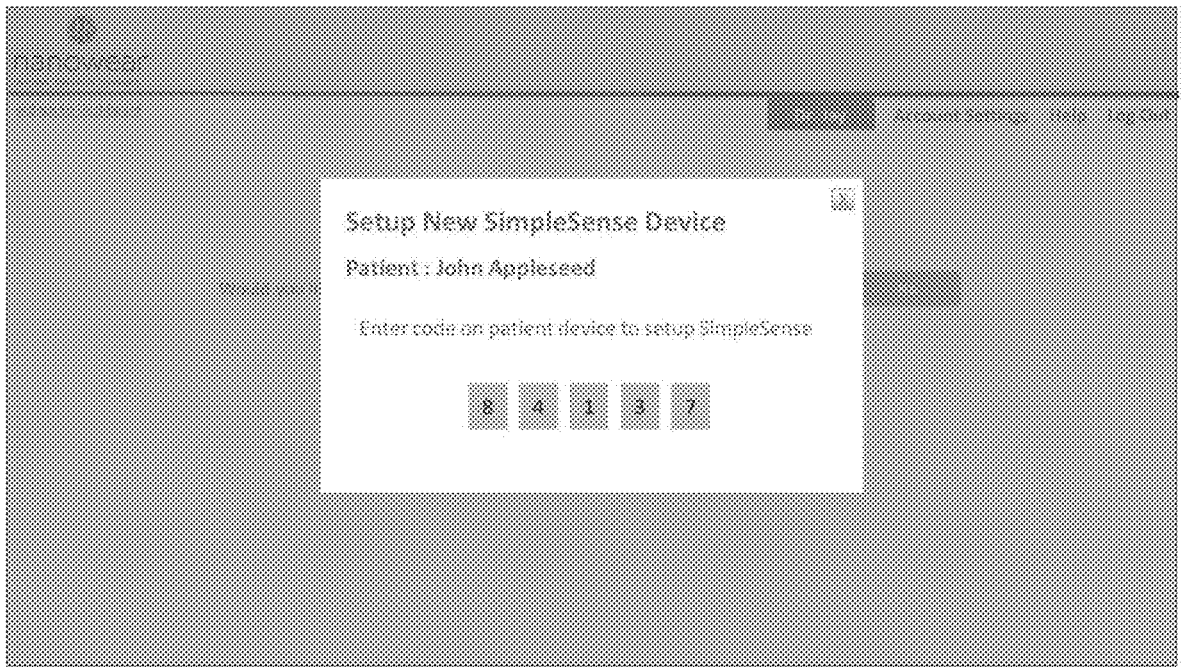
Figure 15:
FIGS. 15(a), 15(b), and 15(c) show an exemplary sequence of screens that are used by a medical professional to setup a patient's smart phone for monitoring of CHF through the SAU (Signal Acquisition Unit).
Figure 15B:
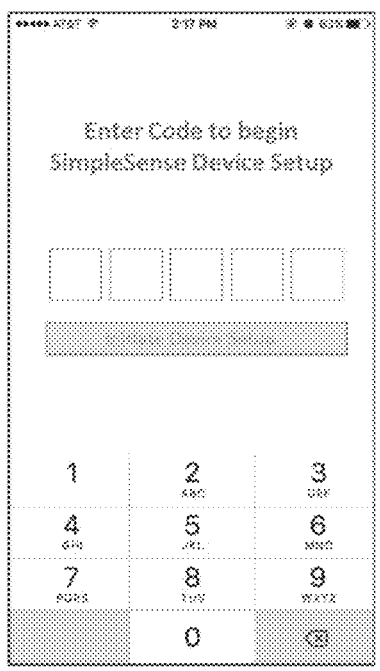
Figure 15C:
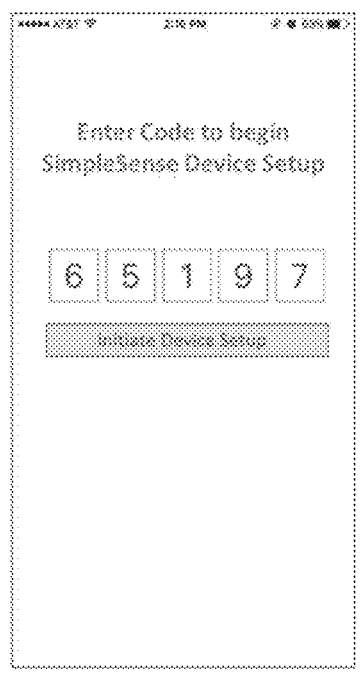
Figure 16:
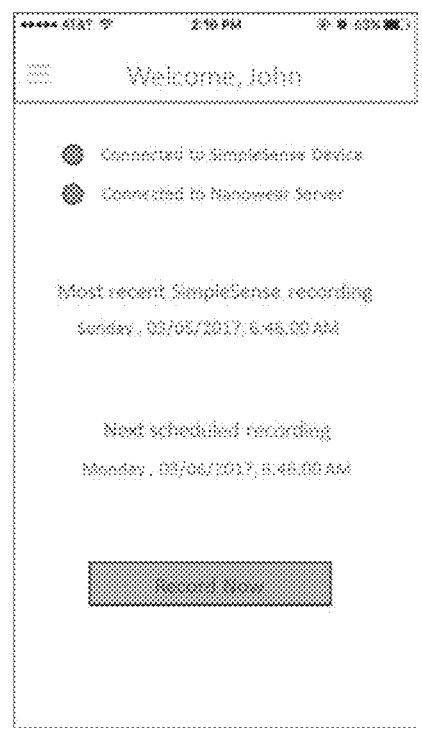
FIG. 16 shows an exemplary user interface for a patient who launches the app after monitoring setup is completed.
Figures 17A, 17B:
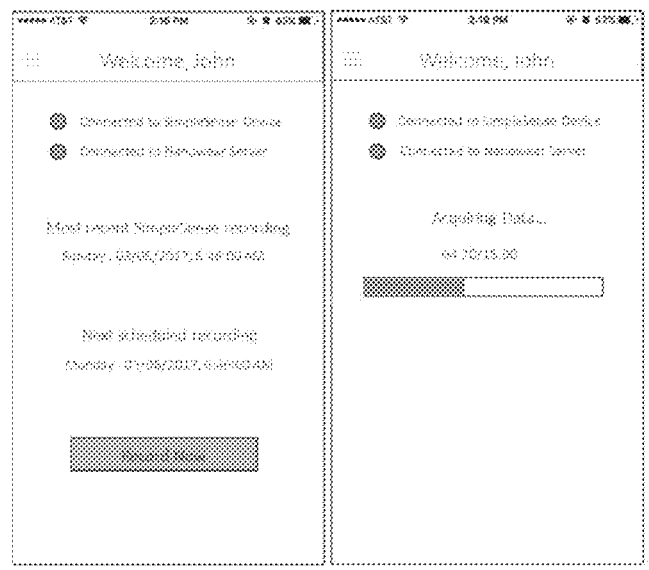
FIGS. 17(a) and 17(b) show an exemplary User interface on smart phone for a patient-initiated recording on the SAU.
Figure 18A:
FIGS. 18(a) and 18(b) show an exemplary User interface wherein data is uploaded from the smart phone 401 to the database services 603.
Figure 18B:
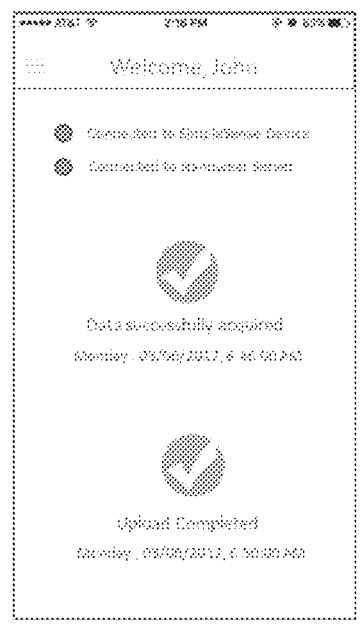

FIGS. 12-15 illustrate an exemplary implementation of user interface that is accessible to an end user or patient while setting up a SAU for CHF monitoring. FIG. 12 is a log in screen for accessing web portal. FIG. 13 shows a dashboard screen for user "Dr. Jay", which shows, for each patient of Dr. Jay being monitored, review status, patient name, patient MRN, date monitoring commenced, date of most recent data, compliance percentage, and priority. FIG. 14(*a*) illustrates a screen for inputting patient information, including, name, address, date of birth, doctor, insurance carrier, email, and priority. It also includes a button for initiating synching of the electronic medical record (EMR) of the patient. FIG. 14(*b*) is a screen in which the user can elect to set up a connection to the SAU and smartphone. If the user selects yes in FIG. 14(*b*), a code is displayed as shown in FIG. 14(*c*). As a person of ordinary skill in the art will appreciate, use of such codes is a well known method of set up connection to a remote device such as a smart phone. To connect the device (eg. Smart phone), the user enters the information on the screens shown in FIG. 15(*a*)-(*c*) from a "simplesense" app on the smartphone, including username/password and then the code from FIG. 14(*c*). FIG. 16 shows a screen which confirms that the smartphone is connected to the SAU and to the server. The connection can be managed through the Bluetooth connection manager on the smartphone app and exchange of a handshake message over standard Representational State Transfer (REST) or other Application Programming Interface (API) known to those skilled in the art. If the user selects record (FIG. 17*a*), then the smart phone 50 will instruct the SAU 40 to begin recording through code 504 and then data will be acquired using code 501 (FIG. 17(*b*), FIG. 18(*a*)) , and then uploaded (FIG. 18(*b*)) to the database services code 603 in web server 60.

Figure 19:
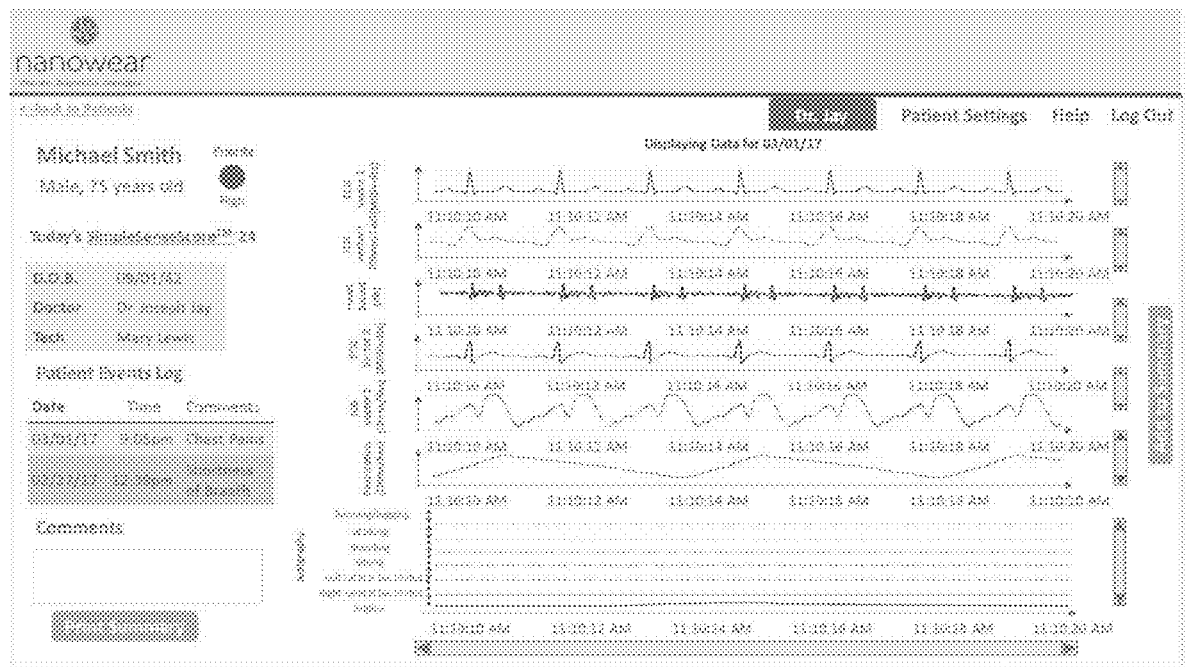
FIG. 19 shows an exemplary user interface implemented on web portal 602 that displays all the data acquired by the SAU as plots.
Figure 20:
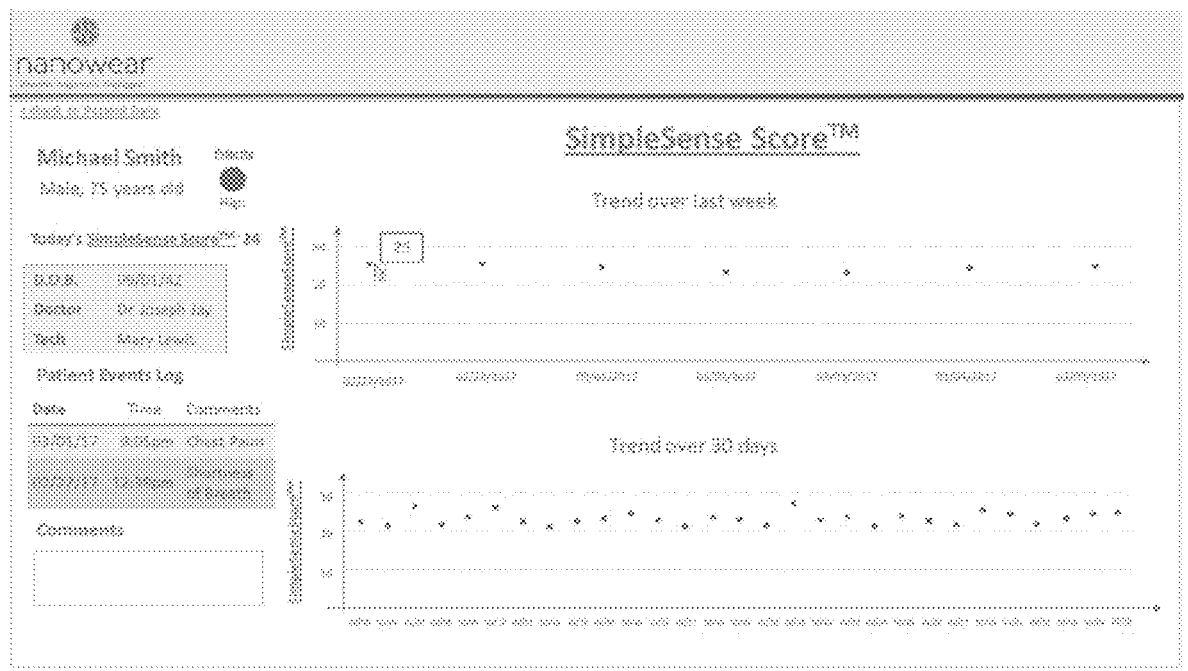
FIG. 20 shows an exemplary user interface for the display of a composite CHF status monitoring metric that is derived from the parameters in Table 1.

FIG. 19 shows the data display for one of Dr. Jay's patients, including the patient name and data from the EMR on the left, and then on the right the data from the harness discussed previously with respect to FIG. 6. Also shown on the left of the display is the "simple sense" score of 24. FIG. 20 is a screen showing the simple sense score over time. The SimpleSense score is a weighted sum of a combination of several features listed in Table 2. The score is a probabilistic predictor that indicates the likelihood of impending hospital emergency admission for a patient with heart failure due to worsening heart failure symptoms.

Figure 21:
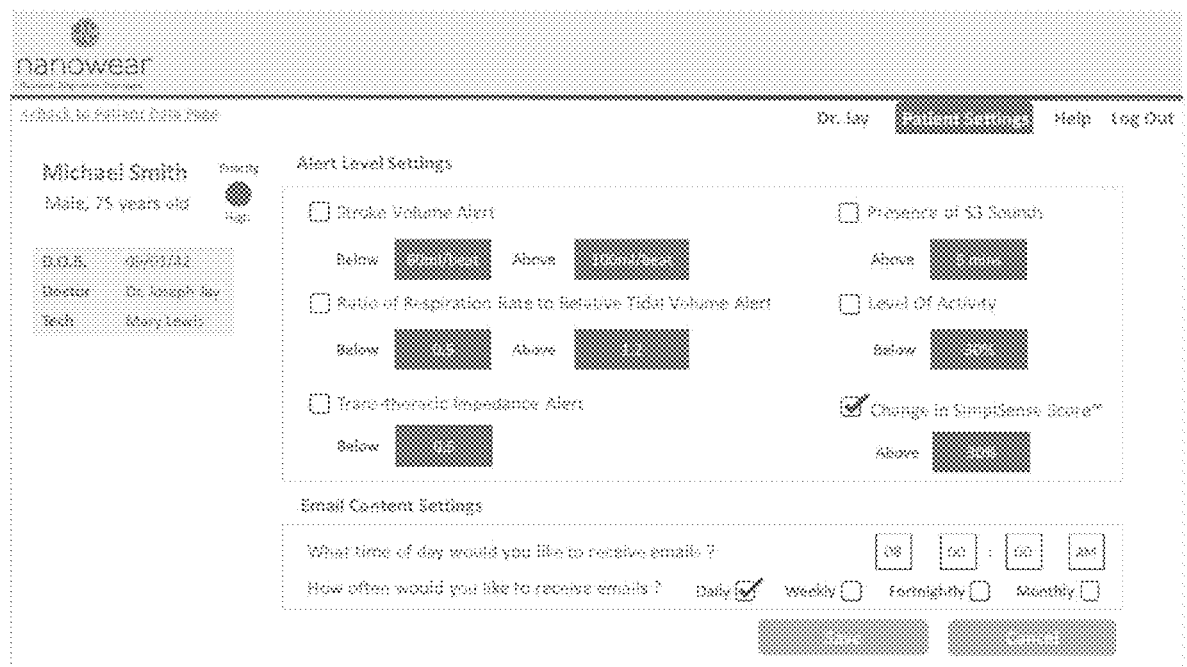
FIG. 21 shows an exemplary user interface wherein the physician can specify alert thresholds for various parameters that are captured by the SAU and computed by step 605 of FIG. 10(a).

FIG. 21 shows a patient setting screen which allows Dr Jay to set alerts for the patient, including stroke volume alert, ratio of respiration rate to relative tidal volume alert, transthoratic impedance alert, presence of S3 sounds alert, level of activity alert, level of activity alert, change in simple sense alert. Stroke volume is a direct measure of the amount of blood the heart is able to pump in one cardiac cycle with is a metric used to assess heart failure patients. Ratio of respiration rate to relative tidal volume is a measure of shortness of breath. Presence of S3 heart sounds indicates that there is resistance to the filling of the left ventricle, which in turn lowers the stroke volume. Level of activity changes are an indirect indicator of the patient's exercise tolerance. Change in Simplesense is an indicator of the rapidity of change in the patient's condition.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

Obvious variants of the disclosed embodiments are within the scope of the description and the claims that follow.

All references cited herein, as well as text appearing in the figures and tables, are hereby incorporated by reference in their entirety for all purposes to the same extent as if each were so individually denoted.

What is claimed is:

1. A wearable, textile-based harness, consisting of:
   an adjustable elastic horizontal band, wherein: the band is configured for wrapping proximate to a body portion of a wearer around the thoracic cage region and for passing over a xyphoid process and a thoracic cage between 5th and 6th ribs positions;
   a plurality of sensors configured for location along the band, wherein the plurality of sensors include a first and second sensor configured for location to the right of the heart of the wearer between the lower-right of the thoracic cage between 5th and 6th ribs positions and a third and fourth sensor configured for location to the left of the heart of the wearer between the lower-left of the thoracic cage between 5th and 6th ribs positions,
   wherein the first sensor is configured for approximate location below a right armpit and the third sensor is configured for approximate location below a left armpit and wherein the second sensor is located downward and to the heart side of the first sensor and the fourth sensor is located downward and to the heart side of the third sensor.

2. The band of claim 1, wherein the first, second, third and fourth sensors are configured for location on a front side of the band.

3. The band of claim 1, wherein the first, second, third and fourth sensors are configured for location on a back side of the band.

4. The band of claim 1, wherein the band is adjustable via fasteners.

5. The band of claim 1, wherein band is made of an elastic fabric, and wherein each of the plurality of sensors are located at sensor locations on the elastic fabric, and wherein, at one or more of the sensor locations, a non-elastic material is fixed on the elastic fabric, an elastomeric material is fixed on the non-elastic material, and one or more of the sensors is fixed on the elastomeric material.

6. The band of claim 1, wherein the plurality of sensors include at least one textile based nanosensor comprising vertically standing nanofilaments.

7. The band of claim 1, wherein upon wearing the band, the first and second plurality of sensors are placed in contact with skin of wearer with a sensor-skin pressure in the range of 60 to 250 gram-force.

8. A sleep disorder management system comprising:
   a wearable, textile-based, adjustable elastic horizontal band wherein the band is configured for wrapping proximate to a body portion of a wearer around the thoracic cage region and for passing over a xyphoid process and a thoracic cage between 5th and 6th ribs positions;
   a plurality of sensors configured for location along the band, wherein the plurality of sensors include a first and second sensor configured for location to the right of the heart of the wearer between the lower-right of the thoracic cage between 5th and 6th ribs positions and a third and fourth sensor configured for location to the left of the heart of the wearer between the lower-left of the thoracic cage between 5th and 6th ribs positions, wherein the first sensor is configured for approximate location below a right armpit and the third sensor is configured for approximate location below a left armpit and wherein the second sensor is located downward and to the heart side of the first sensor and the fourth sensor is located downward and to the heart side of the third sensor;
   a signal acquisition unit including an analog front end circuit, a processor, a wireless module, and a power supply, the SAU receiving signals from the plurality of sensors, generating, from the signals, an ECG signal and an ICG signal, and wirelessly transmitting at least the ECG signal and the ICG signal to a remote computing device.

9. The system of claim 8, further comprising the remote computing device, the remote computing device including a processor and computer readable media having stored thereon computer executable process steps operative to control the processor to display on a display screen a graph of the ICG and ECG signals as a function of time.

10. The system of claim 8, wherein the plurality of sensors include at least one textile based nanosensor comprising vertically standing nanofilaments.

11. The system of claim 8, wherein at least one IMU is used to measure sleeping position, activity and posture.

12. A method of detecting changes in patterns of breathing associated with sleep disordered breathing comprising:
   providing a wearable, textile-based, adjustable elastic horizontal band, wherein when worn by the human, the band wraps proximate to a body portion of the human around the thoracic cage region and passes over a xyphoid process and a thoracic cage between 5th and 6th ribs positions, said band including a plurality of sensors located along the band, wherein the plurality of sensors include a first and second sensor located on a front side of the band to the right of the heart of the human between the lower-right of the thoracic cage between 5th and 6th ribs positions and a third and fourth sensor located on the front side of the band to the left of the heart of the human between the lower-left of the thoracic cage between 5th and 6th ribs positions, wherein the second sensor is located downward and to the heart side of the first sensor and the fourth sensor is located downward and to the heart side of the third sensor and wherein the first sensor is configured for approximate location below a right armpit and the third sensor is configured for approximate location below a left armpit, wherein upon wearing the textile-based band, the plurality of sensors are placed in contact with skin of the human; and measuring simultaneously the respiration and ECG of the human to detect changes in patterns of breathing associated with sleep disordered breathing.

13. The method of claim 12, further comprising displaying on a display screen a graph of the ECG signal and respiration as a function of time.

14. The method of claim 12, further comprising generating a plurality of parameters from the ECG and ICG vectors, including:
   atrial electrical activity from at least one of the ECG vectors;
   ventricular electrical activity from at least one of the ECG vectors;
   PR interval of atrio-ventricular conduction interval from at least one of the ECG vectors;
   QRS measures from at least one of the ECG vectors;
   ST-T measures from at least one of the ECG vectors;
   cardiac output from at least one of the ICG vectors;
   stroke volume from at least one of the ICG vectors;
   cardio-vascular pressures from at least one of the ICG vectors;
   pulmonary pressures from at least one of the ICG vectors;
   minute ventilation from at least one of the ICG vectors;
   shortness of breath from at least one of the ICG vectors;
   exercise tolerance from at least one of the ECG and ICG vectors;
   heart rate from at least one of the ECG vectors;
   heart rhythm from at least one of the ECG vectors;
   transthoracic impedance from at least one of the ICG vectors; and
   ejection fraction from at least one of the ICG vectors.

15. The method of claim 12, wherein the sleep disordered breathing is selected from the group consisting of central and/or obstructive sleep apnea, hypopnea, and arousal due to apnea events in a human.

16. A method of determining sleep state or wakefulness using the combination of posture, activity, respiration, and heart rate as a function of time in a human, comprising:
   providing a wearable, textile-based, adjustable elastic horizontal band, wherein when worn by the human, the band wraps proximate to a body portion of the human around the thoracic cage region and passes over a xyphoid process and a thoracic cage between 5th and 6th ribs positions, said band including a plurality of sensors located along the band, wherein the plurality of sensors include a first and second sensor located on a front side of the band to the right of the heart of the human between the lower-right of the thoracic cage between 5th and 6th ribs positions and a third and fourth sensor located on the front side of the band to the left of the heart of the human between the lower-left of the thoracic cage between 5th and 6th ribs positions, wherein the second sensor is located downward and to the heart side of the first sensor and the fourth sensor is located downward and to the heart side of the third sensor and wherein the first sensor is configured for approximate location below a right armpit and the third sensor is configured for approximate location below a left armpit, wherein upon wearing the textile-based band, the plurality of sensors are placed in contact with skin of the human; and measuring simultaneously the respiration and ECG, posture and activity of the human to detect changes in patterns of breathing, all as a function of time, to determine sleep state or wakefulness.

17. The method of claim 16, further comprising displaying on a display screen a graph of the ECG signal, respiration, posture and activity as a function of time.

18. The method of claim 16, further comprising generating a plurality of parameters from the ECG and ICG vectors, including:
   atrial electrical activity from at least one of the ECG vectors;
   ventricular electrical activity from at least one of the ECG vectors;
   PR interval of atrio-ventricular conduction interval from at least one of the ECG vectors;
   QRS measures from at least one of the ECG vectors;
   ST-T measures from at least one of the ECG vectors;
   cardiac output from at least one of the ICG vectors;
   stroke volume from at least one of the ICG vectors;
   cardio-vascular pressures from at least one of the ICG vectors;
   pulmonary pressures from at least one of the ICG vectors;
   minute ventilation from at least one of the ICG vectors;
   shortness of breath from at least one of the ICG vectors;
   exercise tolerance from at least one of the ECG and ICG vectors;
   heart rate from at least one of the ECG vectors;
   heart rhythm from at least one of the ECG vectors;
   transthoracic impedance from at least one of the ICG vectors; and
   ejection fraction from at least one of the ICG vectors.

* * * * *